United States Patent
Brandeis

(10) Patent No.: US 9,566,070 B2
(45) Date of Patent: Feb. 14, 2017

(54) DEVICE AND METHOD FOR TREATING A VESSEL

(71) Applicant: V.V.T. Med Ltd., Kfar-Saba (IL)

(72) Inventor: Zeev Brandeis, Rosh HaAyin (IL)

(73) Assignee: V.V.T. Med Ltd., Kfar-Saba (IL)

( * ) Notice: Subject to any disclaimer, the term of this patent is extended or adjusted under 35 U.S.C. 154(b) by 0 days.

(21) Appl. No.: 14/040,834

(22) Filed: Sep. 30, 2013

(65) Prior Publication Data
US 2014/0031851 A1     Jan. 30, 2014

Related U.S. Application Data

(63) Continuation of application No. 11/659,083, filed as application No. PCT/US2005/027351 on Aug. 1, 2005, now Pat. No. 8,545,532.

(60) Provisional application No. 60/626,874, filed on Nov. 12, 2004, provisional application No. 60/592,397, filed on Aug. 2, 2004.

(51) Int. Cl.
*A61F 2/06* (2013.01)
*A61B 17/12* (2006.01)
*A61B 17/00* (2006.01)

(52) U.S. Cl.
CPC ... *A61B 17/12109* (2013.01); *A61B 17/12022* (2013.01); *A61B 17/12045* (2013.01); *A61B 17/12136* (2013.01); *A61B 17/12172* (2013.01); *A61B 2017/00867* (2013.01); *A61B 2017/1205* (2013.01); *A61B 2017/12054* (2013.01)

(58) Field of Classification Search
CPC .................. A61B 17/12022; A61B 17/12045; A61B 17/12136; A61B 17/12172; A61B 17/12109; A61B 2017/00867

USPC ....... 606/200, 157, 159, 192, 198, 195, 191; 623/1.11

See application file for complete search history.

(56) References Cited

U.S. PATENT DOCUMENTS

| | | | |
|---|---|---|---|
| 4,723,549 A | 2/1988 | Wholey et al. | |
| 5,683,411 A | 11/1997 | Kavteladze et al. | |
| 5,725,552 A * | 3/1998 | Kotula et al. | 606/213 |
| 5,755,769 A | 5/1998 | Richard et al. | |
| 5,895,410 A | 4/1999 | Forber et al. | |
| 6,071,292 A | 6/2000 | Makower et al. | |

(Continued)

FOREIGN PATENT DOCUMENTS

| | | |
|---|---|---|
| CN | 1216929 | 5/1999 |
| DE | 4101935 | 7/1992 |

(Continued)

OTHER PUBLICATIONS

Invitation Pursuant to Rule 63(1) EPC Dated Feb. 18, 2014 From the European Patent Office Re. Application No. 13196092.4.

(Continued)

*Primary Examiner* — Vy Bui

(57) ABSTRACT

A device and method for treating bodily diseases and/or conditions, for example, varicose veins, tumors and aneurysms including for example insertion of a blocking device toward a target destination using a catheter and delivery of sclerosing or other agents to the vessel while maintaining minimal, for example zero pressure in the treatment area. The blocking device may prevent treatment materials, embolisms, debris etc. from entering the upstream section of vessel. The blocking device may include, for example, a cap or other concave shape and may be expandable or extendible towards the vessel walls.

19 Claims, 16 Drawing Sheets

(56) References Cited

U.S. PATENT DOCUMENTS

| | | | |
|---|---|---|---|
| 6,251,122 B1* | 6/2001 | Tsukernik | 606/200 |
| 6,605,102 B1 | 8/2003 | Mazzocchi et al. | |
| 6,638,293 B1* | 10/2003 | Makower et al. | 606/200 |
| 6,645,205 B2 | 11/2003 | Ginn | |
| 6,958,059 B2 | 10/2005 | Zadno-Azizi | |
| 7,128,073 B1* | 10/2006 | van der Burg et al. | 128/887 |
| 2003/0036755 A1 | 2/2003 | Ginn | |
| 2003/0040772 A1 | 2/2003 | Hyodoh et al. | |
| 2003/0093117 A1 | 5/2003 | Saadat | |
| 2004/0078054 A1 | 4/2004 | Biggs et al. | |
| 2009/0216261 A1 | 8/2009 | Brandeis et al. | |

FOREIGN PATENT DOCUMENTS

| | | |
|---|---|---|
| WO | WO 98/26737 | 6/1998 |
| WO | WO 99/07292 | 2/1999 |
| WO | WO 99/12484 | 3/1999 |
| WO | WO 01/72239 | 10/2001 |
| WO | WO 2006/017470 | 2/2006 |

OTHER PUBLICATIONS

Restriction Official Action Dated Oct. 3, 2014 From the US Patent and Trademark Office Re. U.S. Appl. No. 14/040,834.
Requisition by the Examiner Dated Oct. 16, 2013 From the Canadian Intellectual Property Office Re. Application No. 2,575,812.
Communication Pursuant to Article 94(3) EPC Dated Jun. 7, 2013 From the European Patent Office Re. Application No. 05778828.3.
Communication Pursuant to Rules 70(2) and 70a(2) EPC Dated Aug. 17, 2012 From the European Patent Office Re. Application No. 05778828.3.
Examiner's Report Dated Oct. 13, 2011 From the Australian Government, IP Australia Re. Application No. 2005271635.
Examiner's Report Dated Jun. 21, 2010 From the Australian Government, IP Australia Re. Application No. 2005271635.
International Preliminary Report on Patentability Dated Feb. 15, 2007 From the International Bureau of WIPO Re.: Application No. PCT/US2005/027351.
International Search Report Dated Oct. 24, 2006 From the International Searching Authority Re.: Application No. PCT/US05/27351.
Notice of Allowance Dated Dec. 6, 2012 From the US Patent and Trademark Office Re. U.S. Appl. No. 11/659,083.
Notice of Allowance Dated May 24, 2013 From the US Patent and Trademark Office Re. U.S. Appl. No. 11/659,083.
Office Action Dated Mar. 6, 2011 From the Israeli Patent Office Re.: Application No. 181090 and Its Translation Into English.
Office Action Dated Nov. 6, 2009 From the State Intellectual Property Office of the People's Republic of China Re.: Application No. 2005800334463 and Its Translation Into English.
Office Action Dated Aug. 19, 2009 From the Israeli Patent Office Re.: Application No. 181090 and Its Translation Into English.
Office Action Summary in English Dated Jun. 15, 2012 From the Korean Intellectual Property Office (KIPO) Re. Application No. 10-2007-7005149.
Official Action Dated Jun. 8, 2011 From the US Patent and Trademark Office Re. U.S. Appl. No. 11/659,083.
Official Action Dated Apr. 13, 2011 From the US Patent and Trademark Office Re. U.S. Appl. No. 11/659,083.
Official Action Dated Nov. 14, 2011 From the US Patent and Trademark Office Re. U.S. Appl. No. 11/659,083.
Requisition by the Examiner Dated Oct. 5, 2012 From the Canadian Intellectual Property Office Re. Appliation No. 2,575,812.
Requisition by the Examiner Dated Oct. 25, 2011 From the Canadian Intellectual Property Office Re. Application No. 2,575,812.
Response Dated May 3, 2011 to Notice of Reasons for Rejection of Feb. 22, 2011 From the Japanese Patent Office Re. Application No. 2007-524899.
Response Dated May 7, 2010 to Office Action of Aug. 18, 2009 From the Israeli Patent Office Re.: Application No. 181090.
Response Dated Sep. 8, 2011 to Official Action of Jun. 8, 2011 From the US Patent and Trademark Office Re. U.S. Appl. No. 11/659,083.
Response Dated May 12, 2011 to Official Action of Apr. 13, 2011 From the US Patent and Trademark Office Re. U.S. Appl. No. 11/659,083.
Response Dated Jun. 19, 2011 to Examiner's Report of Jun. 21, 2010 From the Australian Government, IP Australia Re. Application No. 2005271635.
Response Dated Aug. 28, 2011 to Office Action of May 8, 2011 From the State Intellectual Property Office of the People's Republic fo China Re. Application No. 201010135950.7.
Response Dated Dec. 29, 2011 to Notice of Reasons for Rejection of Oct. 18, 2011 From the Japanese Patent Office Re. Application No. 2007-524899.
Supplementary European Search Report and the European Search Opinion Dated Jul. 31, 2012 From the European Patent Office Re. Application No. 05778828.3.
Translation of Notice of Reasons for Rejection Dated Oct. 18, 2011 From the Japanese Patent Office Re. Application No. 2007-524899.
Translation of Notice of Reasons for Rejection Dated Feb. 22, 2011 From the Japanese Patent Office Re. Application No. 2007-524899.
Translation of Office Action Dated May 5, 2011 From the State Intellectual Property Office of the People's Republic fo China Re. Application No. 201010135950.7.
Translation of Office Action Dated Mar. 31, 2012 From the State Intellectual Property Office of the People's Republic fo China Re. Application No. 201010135950.7.
Translation of Search Report Dated Nov. 5, 2012 From the State Intellectual Property Office of the People's Republic fo China Re. Application No. 201010135950.7.
Translation of the Notification of Office Action Dated Nov. 5, 2012 From the State Intellectual Property Office of the People's Republic fo China Re. Application No. 201010135950.7.
Written Opinion Dated Oct. 24, 2006 From the International Searching Authority Re.: Application No. PCT/US27351.
Communication Pursuant to Rules 70(2) and 70a(2) EPC and Reference to Rule 39(1) EPC Dated Aug. 11, 2014 From the European Patent Office Re. Application No. 13196092.4.
Partial European Search Report and the European Search Opinion Dated Jul. 4, 2014 From the European Patent Office Re. Application No. 13196092.4.

* cited by examiner (A)

(B)

(C)

(D)

(E)

DEVICE AND METHOD FOR TREATING A VESSEL

RELATED APPLICATIONS

This application is a continuation of U.S. patent application Ser. No. 11/659,083 filed on Apr. 30, 2009, which is a National Phase of PCT Patent Application No. PCT/US2005/027351 filed on Aug. 1, 2005, which claims the benefit of priority under 35 USC §119(e) of U.S. Provisional Patent Application Nos. 60/626,874 filed on Nov. 12, 2004 and 60/592,397 filed on Aug. 2, 2004. The contents of all of the above applications are incorporated by reference as if fully set forth herein.

FIELD OF THE INVENTION

The present invention relates to methods and devices to enable blockage, occlusion and/or treatment of vessels such as blood vessels. Specifically, embodiments of the present invention relate to devices and methods that may block selected segments of veins or arteries.

BACKGROUND OF THE INVENTION

Various bodily diseases and/or conditions, including, for example, tumors, aneurysms and varicose vein expansion, may be caused by malfunction or other problems associated with the veins or arteries that supply or remove blood to/from the treatment areas. For example, the venous system of the lower extremities includes the superficial (greater and lesser saphenous veins) and deep system (popliteal and femoral veins). These two parallel systems are interconnected via perforator veins. One-way valves are present at the junctions between the bifurcation point of the deep and superficial system, at the saphenofemoral and the saphenopopliteal junctions.

Larger varicose veins, e.g., tortuous veins measuring between 2 mm and 2 cm in diameter, and protruding above the surface of the skin, are typically related to valve incompetence either at the saphenofemoral or saphenopopliteal junction. As the venous pressure in the deep system is generally greater than that of the superficial system, valve incompetence leads to increased hydrostatic pressure transmitted to the unsupported superficial vein system, ultimately resulting in varicosities. Clusters of varicosities may appear at the site of perforating vessels, such as the perforating veins of Hunter and Dodd, located in the mid and distal thigh, respectively. This pattern of varicosity is typically associated with incompetence at the saphenofemoral junction.

In some instances, the valvular incompetence may be isolated to a perforator vein, such as the Boyd perforating vein located in the anteromedial calf. These varicosities are often not associated with saphenous vein incompetence since the perforating veins in the lower part of the leg do not communicate directly with the saphenous vein. Although many varicose veins are asymptomatic, symptoms including itching, heaviness, and pain may occur. In addition, varicose veins may be complicated by peripheral edema due to venous insufficiency, hemorrhage, thrombophlebitis, venous ulceration, and chronic skin changes.

Varicose veins are a common condition. In adult western populations visible varicose veins are present in 20-25% of women and 10-15% of men. In most persons, varicose veins do not cause symptoms other than poor cosmetics. Varicose vein surgery is one of the most commonly performed cosmetic procedures in the United States.

Most varicose veins do not require medical treatment (Tapley, et al. 2003). In some cases, however, the circulation may be hindered enough to cause swelling of the foot and ankle, discomfort, a tingling sensation, or a feeling of heaviness. For most people with varicose veins, wearing specially fitted elastic stockings is all that is needed. The stockings should be carefully fitted to the individual, providing the most pressure in the lowest part of the leg. Exercise such as walking or cycling also helps promote better circulation from the lower part of the body. Symptoms often decrease when the legs are elevated periodically, and when prolonged standing is avoided. Varicose veins can usually be treated with non-surgical measures.

When conservative treatment measures fail, additional treatment options typically focus first on identifying and correcting the site of reflux, and second on redirecting venous flow through veins with intact valves. Surgical treatment of varicosities may include controlling the most proximal point of reflux, typically at the saphenofemoral junction, as identified by preoperative Doppler ultrasonography. Surgical ligation and division of the saphenofemoral or saphenopopliteal junction is performed to treat the valvular incompetence. Another surgical treatment includes removal of the refluxing greater and/or lesser saphenous vein from the circulation. The most typical strategy for isolation is vein stripping, which is generally preceded by vein ligation and division. A further surgical treatment includes removal of the varicose tributaries. Strategies for removal include stab avulsion or injection sclerotherapy, either at the time of the initial treatment, or subsequently.

Over the years various different minimally invasive alternatives to ligation and stripping have been investigated, including sclerotherapy, endoluminal radiofrequency ablation and laser ablation. The objective of sclerotherapy is generally to destroy the endothelium of the target vessel by injecting an irritant solution (for example a detergent, osmotic solution, or a chemical irritant), ultimately resulting in the complete obliteration of the vessel. Too little destruction may lead to thrombosis without fibrosis and ultimate recanalization. Too much destruction may lead to vascular dehiscence. The success of the treatment may depend on accurate injection of the vessel, an adequate injectant volume and concentration of sclerosant, and post-procedure compression. Compression theoretically results in direct apposition of the treated vein walls to provide more effective fibrosis and may decrease the extent of the thrombosis formation. Therefore, due to technical limitations, larger veins and very tortuous veins may not be good candidates for sclerotherapy.

While sclerotherapy is an accepted and effective treatment of telangiectatic vessels, it has also been used in the treatment of varicose tributaries without prior ligation, with or without vein stripping. This application of sclerotherapy creates issues regarding its effectiveness in the absence of the control of the point of reflux and isolation of the refluxing saphenous vein. In addition, when the sclerosant is injected into the greater or lesser saphenous vein, sclerotherapy has been investigated as a minimally invasive alternative to vein stripping, either with or without ligation. Since the saphenous vein is not visible with the naked eye, injection is typically guided by ultrasonography, and the combined procedure may be referred to as "echosclerotherapy." Since the greater saphenous vein is larger and deeper than telangiectatic dermal veins, sclerotherapy of this vein raises issues regarding appropriate volume and concentration of the sclerosant and the ability to provide adequate post-procedure compression. Moreover, the use of sclerotherapy, as opposed to the physical removal of the vein with stripping, raises the issue of recurrence due to recanalization.

McDonagh, et al. (2002, 2003) has reported on the effectiveness of ultrasound-guided foam sclerotherapy (comprehensive objective mapping, precise image-guided injection, antireflux positioning and sequential sclerotherapy (COMPASS) technique) in the treatment persons with varicosities of the greater saphenous vein with saphenous vein reflux. Published studies of the COMPASS technique involve relatively short-term follow up. Study subjects were followed for three years, and for only two years after completion of a series of repeat sclerotherapy injections that were administered over one year. In addition, these studies do not include a comparable group of subjects treated with surgery, which has been the primary method of treating incompetent long saphenous veins. Thus, definitive conclusions cannot be made about the durability of results of the COMPASS technique or its effectiveness compared with surgery for treatment of greater saphenous vein varicosities and saphenofemoral incompetence. In addition, published studies of the COMPASS technique come from a single group of investigators.

Published long-term randomized controlled clinical studies have demonstrated that surgery plus sclerotherapy is more effective than surgery alone for treatment of varicosities associated with incompetence of the saphenofemoral junction. Belcaro, et al. (2003) reported on the results from the Venous Disease International Control (VEDICO) trial, the first long-term randomized controlled clinical trial of foam sclerotherapy. The VEDICO trial involved 749 patients with varicose veins and saphenous vein incompetence who were randomly treated by six different approaches: standard sclerotherapy, high-dose sclerotherapy, surgical ligation, stab avulsion, foam sclerotherapy, and combined surgery (ligation or stab avulsion) and high dose sclerotherapy. At 10 years, the occurrence of new veins was 56% for standard sclerotherapy, 51% for foam sclerotherapy, 49% for high-dose sclerotherapy, 41% for stab avulsion, 38% for ligation, and 27% for combined surgery and sclerotherapy.

Belcaro, et al. (2000) reported on the results of a randomized controlled clinical study comparing ultrasound-guided sclerotherapy with surgery alone or surgery combined with sclerotherapy in 96 patients with varicose veins and superficial venous incompetence. Although all approaches were reported to be effective in controlling the progression of venous incompetence, surgery appeared to be the most effective method on a long-term basis, and that surgery combined with sclerotherapy may be more effective than surgery alone. After 10 years follow up, no incompetence of the saphenofemoral junction was observed in both groups assigned to surgery, compared to 18.8 percent of limbs of subjects assigned to ultrasound-guided sclerotherapy. Of limbs treated with ultrasound-guided sclerotherapy, 43.8% of the distal venous systems were incompetent, compared to 36% of limbs of subjects treated with surgery alone, and 16.1% of limbs of subjects treated with surgery plus sclerotherapy.

In recent years, new methods such as ES (endovascular sclerotherapy) and foam sclerotherapy (using ultrasound guidance) have been developed and proposed to improve the safety and efficacy of sclerotherapy for various types of varicose veins. Evidence about these new techniques for treating patients with incompetence of the long saphenous vein is limited, and the place of sclerotherapy as the first treatment for larger varicose veins (saphenous or non-saphenous) remains controversial.

Endoluminal radiofrequency ablation and laser ablation (e.g. VNUS® Closure™ System, Dornier Diode (Medilas D) and Diomed 810 nm surgical laser and EVLT (endovenous laser therapy)) have been investigated as minimally invasive alternatives to vein ligation and stripping. Both radiofrequency energy and laser therapy are similarly designed to damage the intimal wall of the vessel, resulting in fibrosis and ultimately obliteration of a long segment of the vein. Radiofrequency ablation is generally performed by means of a specially designed catheter inserted through a small incision in the distal medial thigh to within 1-2 cm of the saphenofemoral junction. High frequency radio waves (200-300 kHz) are delivered through the catheter electrode and cause direct heating of the vessel wall, causing the vein to collapse. The catheter is slowly withdrawn, closing the vein. Laser ablation is performed similarly. In the case of endoluminal laser therapy, a bare tipped laser fiber is introduced into the greater saphenous vein under ultrasound guidance; the laser is activated and slowly removed along the course of the saphenous vein.

Such catheters may generally treat veins with diameters that range from 2 to 12 mm. Each catheter may have a microthermocouple to monitor vein wall temperature. In practice, the catheter with its electrodes sheathed, is passed either prograde or retrograde through a venipuncture or through direct surgical exposure of the saphenous vein. The catheter position may be confirmed by ultrasound imaging, and exsanguination of the vein may be accomplished by external elastic wrapping (Esmarch bandaging) or large-volume, very dilute local anesthesia (tumescent technique).

Perhaps the most serious complication of varicose vein surgery, or other vein blockage surgery, is deep venous thrombosis with or without pulmonary embolization. In a number of early reports of varicose vein surgery and minimally invasive endoluminal therapy, the incidence of pulmonary embolization has ranged from 0.4% to 1. A less serious but troublesome complication is dysfunction in the territory of the greater saphenous nerve. This was found in 12.5% of limbs treated by endoluminal therapy.

Subfascial endoscopic perforator vein surgery (SEPS) is a minimally invasive endoscopic procedure that eliminates the need for a large incision in the leg. It has been explored as an alternative to the traditional open surgical treatment of chronic venous insufficiency. The aim of the procedure is to interrupt incompetent medial calf perforating veins to reduce venous reflux and decrease ambulatory venous hypertension in critical areas above the ankle where venous ulcers most frequently develop. Kalra and Gloviczki (2002) stated that available evidence confirmed the superiority of SEPS over open perforator ligation, but do not address its role in the surgical treatment of advanced chronic venous insufficiency (CVI) and venous ulceration. Ablation of superficial reflux by high ligation and stripping of the greater saphenous vein with avulsion of branch varicosities is concomitantly performed in the majority of patients undergoing SEPS. The clinical and hemodynamic improvements attributable to SEPS thus are difficult to ascertain. As with open perforator ligation, clinical and hemodynamic results are better in patients with primary valvular incompetence (PVI) than in those with the post-thrombotic (PT) syndrome.

Contraindications for SEPS include associated arterial occlusive disease, infected ulcer, a non-ambulatory patient, and a medically high-risk patient. Diabetes, renal failure, liver failure, morbid obesity, ulcers in patients with rheumatoid arthritis, or scleroderma, and presence of deep vein obstruction at the level of the popliteal vein or higher on pre-operative imaging are relative contraindications. Patients with extensive skin changes, circumferential large ulcers, recent deep vein thrombosis, severe lymphedema, or large legs may not be suitable candidates (Kalra and Gloviczki, 2002).

BRIEF DESCRIPTION OF THE DRAWINGS

The principles and operation of the system, apparatus, and method according to the present invention may be better understood with reference to the drawings, and the following description, it being understood that these drawings are given for illustrative purposes only and are not meant to be limiting, wherein.

Figure 1:
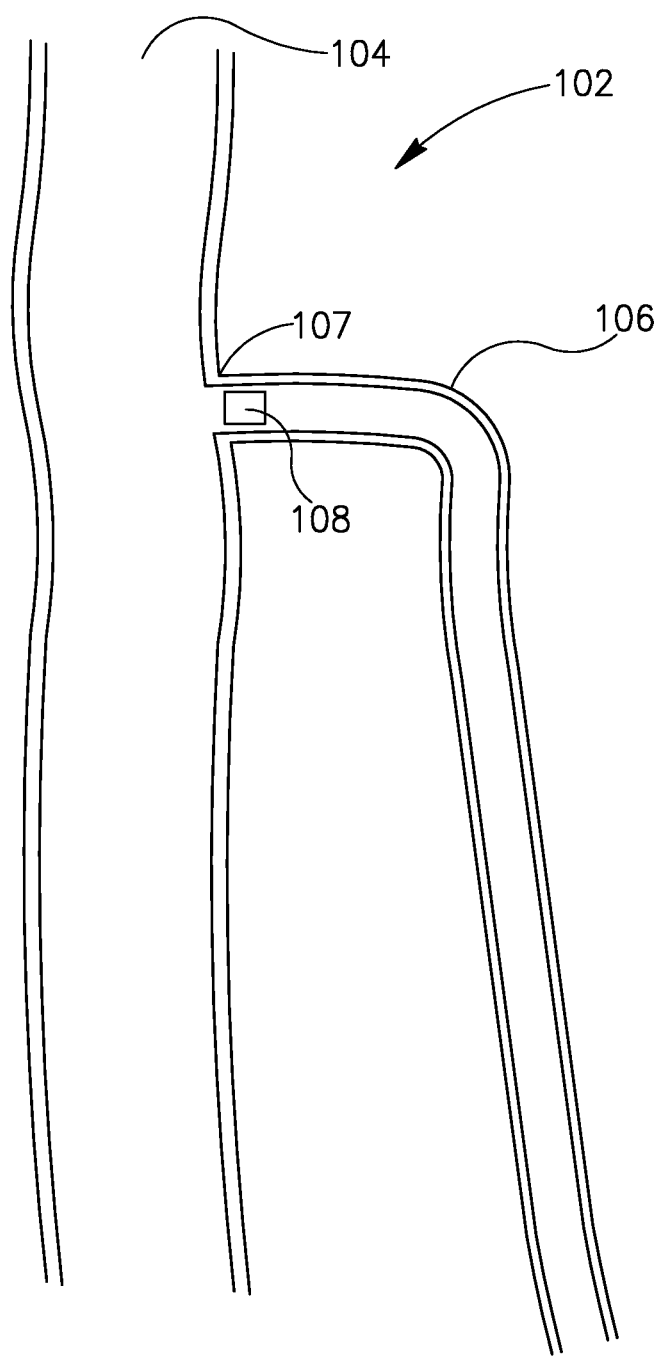
FIG. 1 is a schematic illustration of a vessel closure device in a bifurcated vessel, according to an embodiment of the present invention.

It will be appreciated that for simplicity and clarity of illustration, elements shown in the drawings have not necessarily been drawn to scale. For example, the dimensions of some of the elements may be exaggerated relative to other elements for clarity. Further, where considered appropriate, reference numerals may be repeated among the drawings to indicate corresponding or analogous elements throughout the serial views.

DETAILED DESCRIPTION OF THE INVENTION

The following description is presented to enable one of ordinary skill in the art to make and use the invention as provided in the context of a particular application and its requirements. Various modifications to the described embodiments will be apparent to those with skill in the art, and the general principles defined herein may be applied to other embodiments. Therefore, the present invention is not intended to be limited to the particular embodiments shown and described, but is to be accorded the widest scope consistent with the principles and novel features herein disclosed. In other instances, well-known methods, procedures, and components have not been described in detail so as not to obscure the present invention.

Embodiments of the invention may include an intraluminal device configured to treat complications in vessels, for example bifurcated varicose veins or other damaged vessels, lumen, etc., by selectively blocking off at least part of a vessel using a typically minimally invasive technique. For example, a predetermined region (e.g., the saphenofemoral region) of a bifurcated vein may be blocked off or occluded, and treated typically without harming the non-blocked off region of the vessel. The blocked off section of the vessel may be treated using, for example, ligation, heat and/or sclerosing or other suitable agents. Other lumens may be occluded or blocked using various embodiments of the present invention.

Reference is now made to FIG. 1, which schematically illustrates a simplification of part of the human venus system, including a bifurcated vessel 102. A saphenous vein 106 extends into a femoral vein 104, via saphenofemoral junction 107. A vessel blocking device 108, as is described in detail below, may be deployed in vessel 102, for example, proximal to the saphenofemoral junction 107, or at other suitable location, to block off at least a part of vessel 106. For example, the upstream section of a vein may be blocked off to enable treatment and/or destruction of the blocked portion and/or upstream section of the vein.

Figure 2:
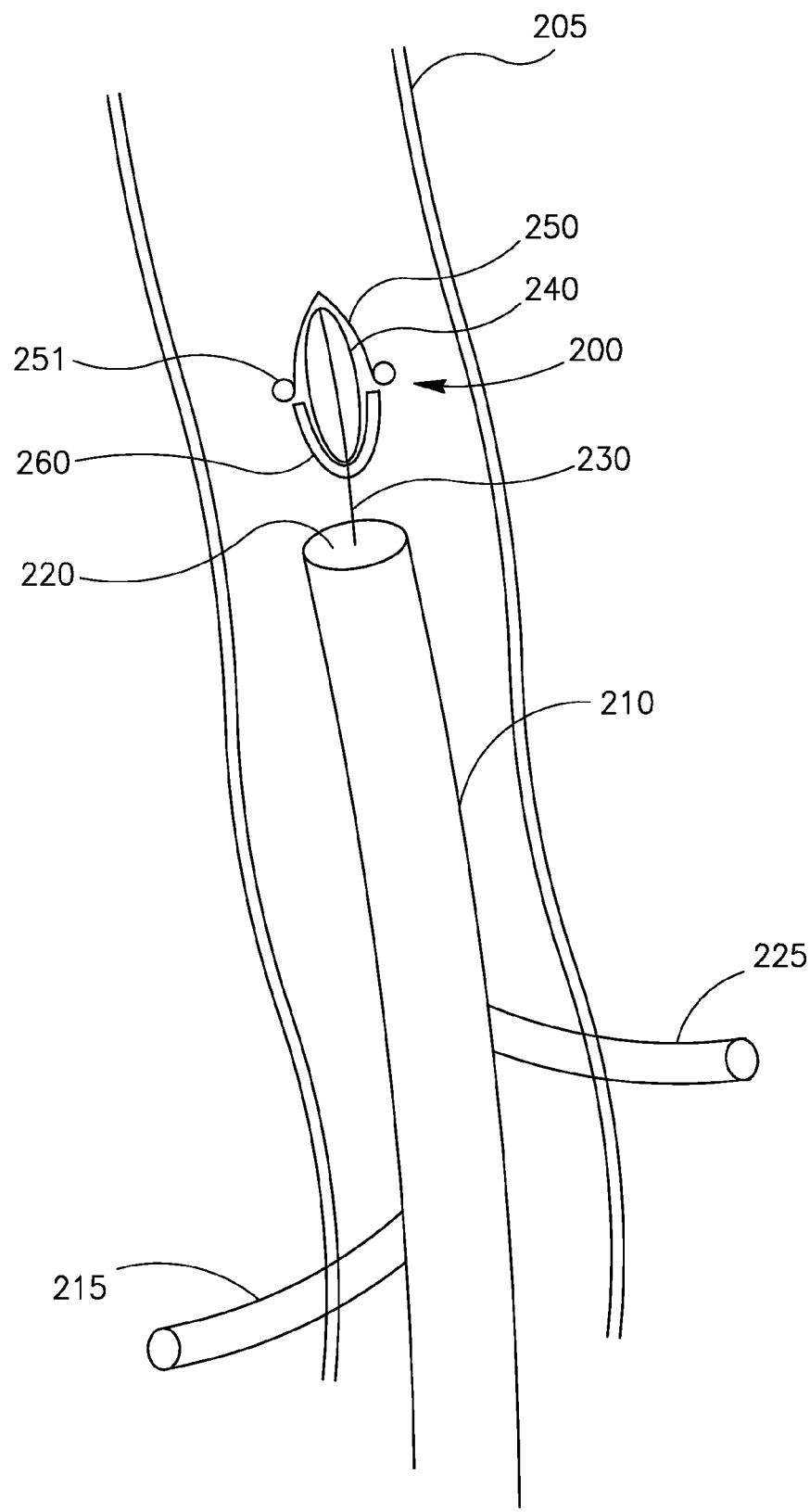
FIG. 2 is a schematic illustration of a catheter delivery of a vessel blocking device, according to an embodiment of the present invention.

Reference is made to FIG. 2, which schematically illustrates a catheter delivery of a vessel blocking device, according to an embodiment of the present invention. Vessel blocking device 200 may be inserted, for example, into a target vessel 205 that requires treatment, for example, a bifurcated vessel or an occluded blood segment that is to be blocked and/or otherwise treated. Such insertion of device 200 may be implemented, for example, using an insertion device such as a catheter 210, which may include, for example, a guidewire 230, to help guide device 200 to a selected location. Other insertion devices and methods may be used. Catheter 210 may include for example a drug dispensing mechanism 215, to enable delivery of a pharmaceutical compound, medication, solution, foam or another suitable agent, such as for example a sclerosing agent, to a target area, via catheter 210. Catheter 210 may include a proximal end (not shown, typically towards or at the control end of the catheter 210) and a distal tip 220. Proximal and distal when use herein are relative terms, typically relative to the control end or holding end of catheter 210; e.g., proximal is nearer the control or external end. The control end (e.g. the proximal end) may be used for holding and operating catheter 210, for example, by a doctor or a health professional. The distal tip 220 may be located after insertion in proximity to the blocking and/or treatment area. Vessel blocking device 200 may include one or more inflatable balloons 240, which may be remotely inflated and/or deflated, for example, by inputting and/or extracting gas and/or liquid via for example an inflation/deflation channel 225. Other or different channels may be used. Other suitable expansion or pressure application elements, other than balloons, may be used. Vessel blocking device 200 may include an extendable or expandable cover or cap 250 that may be extended or expanded so as to block a vessel. The term "cap" as used herein may encompass, for example, a blocking device, shield, plug, stopper, choke or other device or apparatus to plug up, block or occlude, either partially or completely, a selected lumen or vessel. Cap 250 may be concave or bowl shaped and may include a rim 251. Cap 250 may be expandable so that rim 251 may extends outwards towards vessel walls when, for example, a pressure is provided inside. For example, balloons 240 may be inflated, thereby pressuring cap 250 to extend towards the walls of a vessel 205. Cap 250 may be constructed from silicon, plastic, rubber, metal or any other suitable material or combinations of materials. For example, cap 250 may be a flexible structure that may be extended, expanded, retracted, shrunk etc. within a vessel or lumen. More than one cap may be used; e.g., caps placed narrow end to narrow end, or wide end to wide end, may be used.

Vessel blocking device 200 may include a base 260, for example, constructed from stainless steel, rubber, mesh or other suitable materials, to enable stabilizing of cap 250 in a selected location and/or permanent or semi-permanent strengthening of vessel blocking device 200. Base 260 may be mechanically bonded to a portion of cap 250 and/or balloons 240 with, for example, glue, clips, grooves or other suitable bonding mechanisms. Base 260 may enclose balloons 240, cap 250, or may be alternatively arranged to appropriately support cap 250 and/or balloons 240. Balloons 240 may be disposed between cap 250 and the base 260. Base 260 and/or cap 250 may partially surround balloon 250. Vessel blocking device 200 may include an expansion element (e.g., a balloon, a spring, a stent like mechanism, etc.) disposed between cap 250 and base 260 to increase in pressure in the inner portion of the cap to cause the cap to expand outwards towards the vessel walls. Base 260 may also be cap shaped—e.g., two caps may be connected, either at their narrow ends or wide ends. Base 260 may be for example spherical, elliptical, rounded or flat, or may have other suitable geometrical or non-geometrical shapes to enable strengthening or stabilizing of cap 250 and/or balloons 240 in vessel 205. Base 260 may be extended or expanded outwards towards walls of vessel 205, by, for example, inflation of balloons 240 and/or extension of cap 250. Vessel blocking device 200 may be located at the distal tip 220 of the insertion device, for example, catheter 210, and cap 250 may be distal to catheter 210 relative to the cap. Balloon 240 may be disposed between cap 250 and base 260.

Vessel blocking device 200 may be disconnected from catheter 210 or another insertion unit and unnecessary elements of vessel blocking device 200 and/or other elements from vessel 205 may be removed together with catheter 210 from a body, leaving required elements of vessel blocking device 200 in place in vessel 205. For example, after blocking of a vessel has been inserted or implemented by cap 250 and/or base 260, guidewire 230, balloons 240 and/or other non-required elements may be extracted from a vessel 205, via for example catheter 210. Vessel blocking device 200 may enable a total blockage of vessel 205 to be maintained, such that, for example, treatments executed in a section of vessel 205 may be isolated in a selected area defined by cap 250 and/or base 260 and may thereby prevent treatment materials, embolisms, debris etc. from entering the upstream section of vessel 205. For example, vessel 205 may be partially or completely blocked by vessel blocking device 200 while at least a portion of vessel 205 is treated, for example, using sclerotherapy and/or ligation or other treatments, thereby preventing embolisms, debris, pharmaceutical agents and/or other hazardous materials from flowing upstream through vessel 205, for example, to the brain, heart or other vital organs.

Figure 3A:
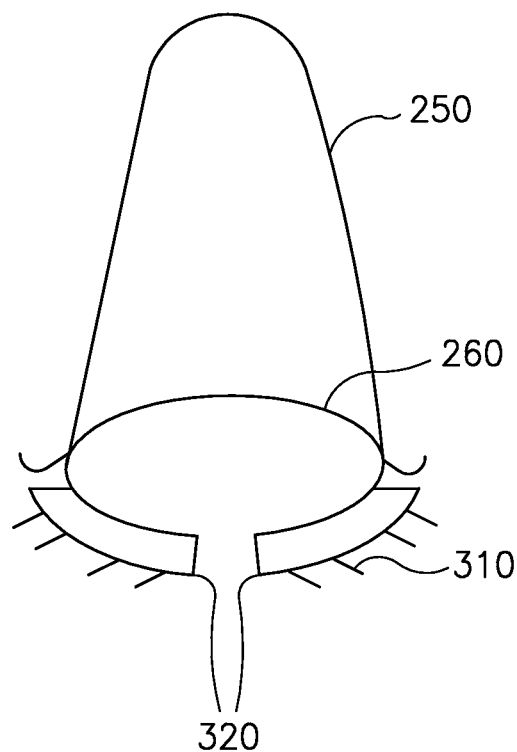
FIGS. 3A-3E are schematic illustrations of vessel blocking devices with different types of anchoring mechanisms, according to some embodiments of the present invention.
Figure 3B:
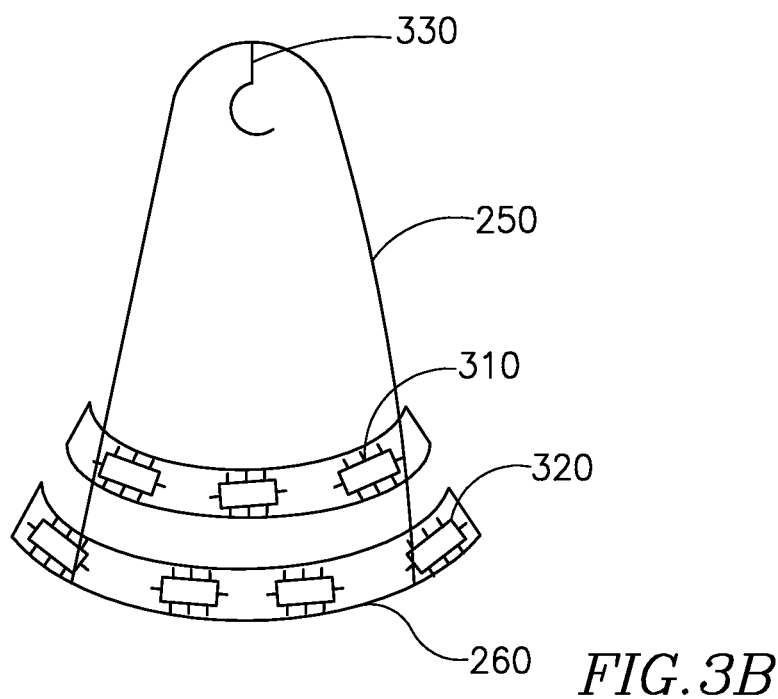

Reference is made to FIGS. 3A and 3B which schematically illustrate types of anchoring mechanisms of vessel blocking devices according to some embodiments of the invention. Base 260 may include one or more anchoring mechanisms 310, for example spikes, hooks or any other suitable shapes or mechanisms placed on a substrate 320. Anchoring mechanisms 310 may be made of for example medical grade rubber, metal, or other suitable materials, as known in the art, or from other suitable materials. Anchoring mechanisms 310 may have varying shapes and arrangements, for example, they may be shaped as arrays of straight spikes, angles spikes, twisted spikes etc. Any suitable combination of spike types, shapes and angles etc. may be used, in any suitable combination, to enable suitable anchoring of cap 250 to vessel wall 205. Anchoring mechanisms 310 may be located on a single substrate 320 on base 260, or may be located on a plurality of separate substrates, to enable greater flexibility when base 260 is extended. Other structures or configurations for anchoring or holding may be used. In some embodiments, specific anchoring mechanisms need not be used. For example pressure or friction may be used for anchoring.

In some embodiments anchoring mechanisms 310 may be associated with and/or connected to cap 250 and/or base 260, optionally enabling cap 250 and base 260, individually and/or in combination to anchor with the walls of vessel 205.

As can be seen with reference to FIG. 3B, cap 250 may include a pullable mechanism or an attachment mechanism 330, for example, a hook shaped mechanism or other suitable mechanism to enable extraction of device 200 from vessel 205, according to some embodiments of the present invention. For example, if it is required device 200 may be extracted from vessel 205 by using, for example, an extraction hook or wire etc. associated with catheter 210 or other insertion mechanism to hook onto or otherwise connect with device 200 at pullable mechanism 330, and extract device 200. Balloons 240 may be dilated before extraction of device 200, and may optionally be extracted via catheter 210. Further, the extraction of device 200 backwards, against the flow of blood in the vessel may enable relatively easily disengagement of anchoring mechanisms 310, since the direction of extraction may be counter the direction of engagement of anchor mechanisms 310.

Figure 3C:
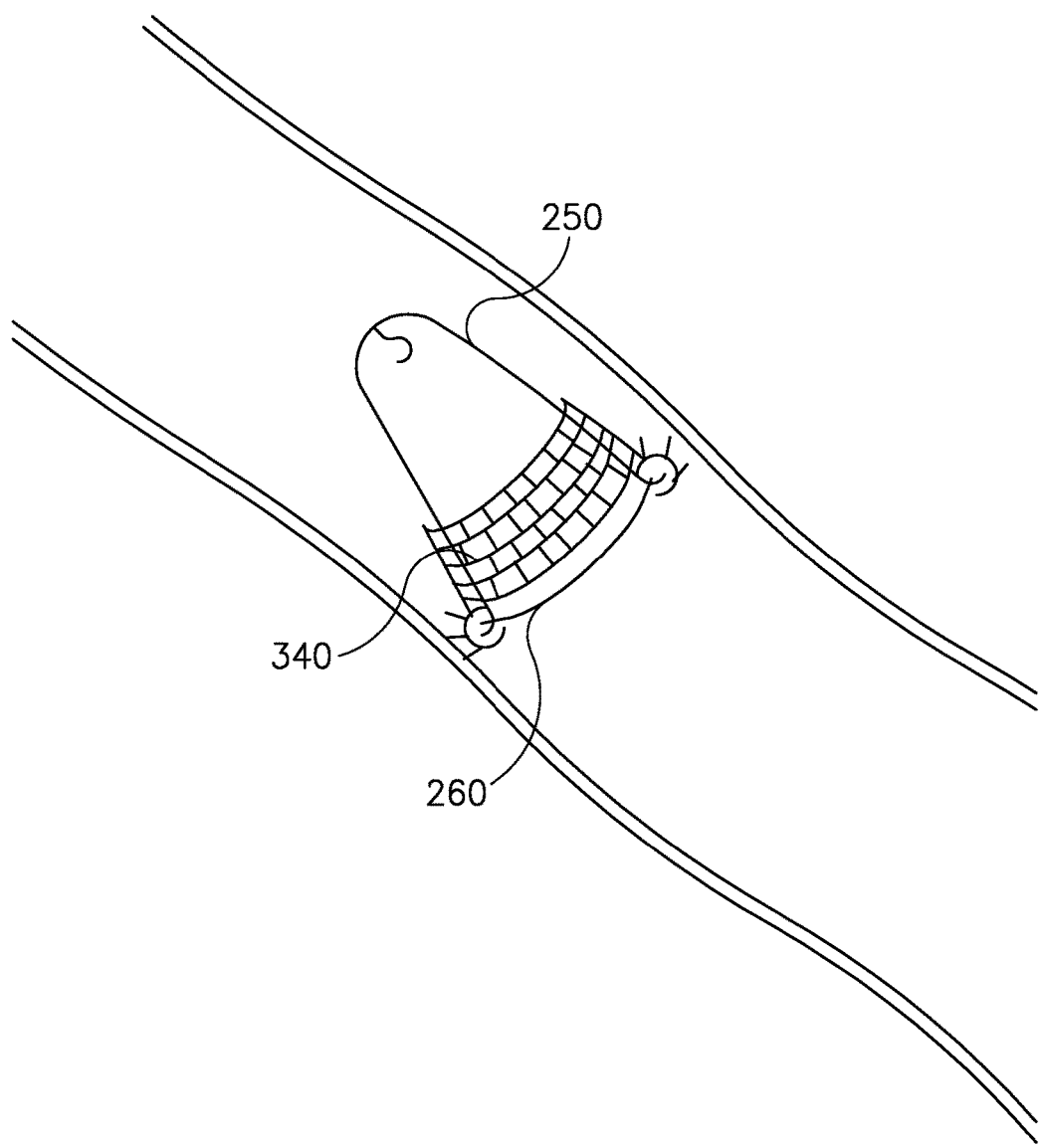

Reference is now made to FIG. 3C, wherein a meshed or stent-like mechanism 340 may enclose at least a portion of cap 250 and/or base 260, according to some embodiments of the present invention. Stent-like mechanism 340 may be expanded by balloons 240 and/or cap 250, optionally providing support to vessel blocking device 200. Stent-like mechanism 340 may include one or more anchoring mechanisms 310 for anchoring vessel blocking device 200 into the walls of a vessel when stent-like mechanism 340 is expanded sufficiently. Stent-like mechanism 340 may be constructed from metal or other suitable materials. Stent-like mechanism 340 may be glued or otherwise bonded or connected to cap 250 and/or base 260.

Figure 3D:
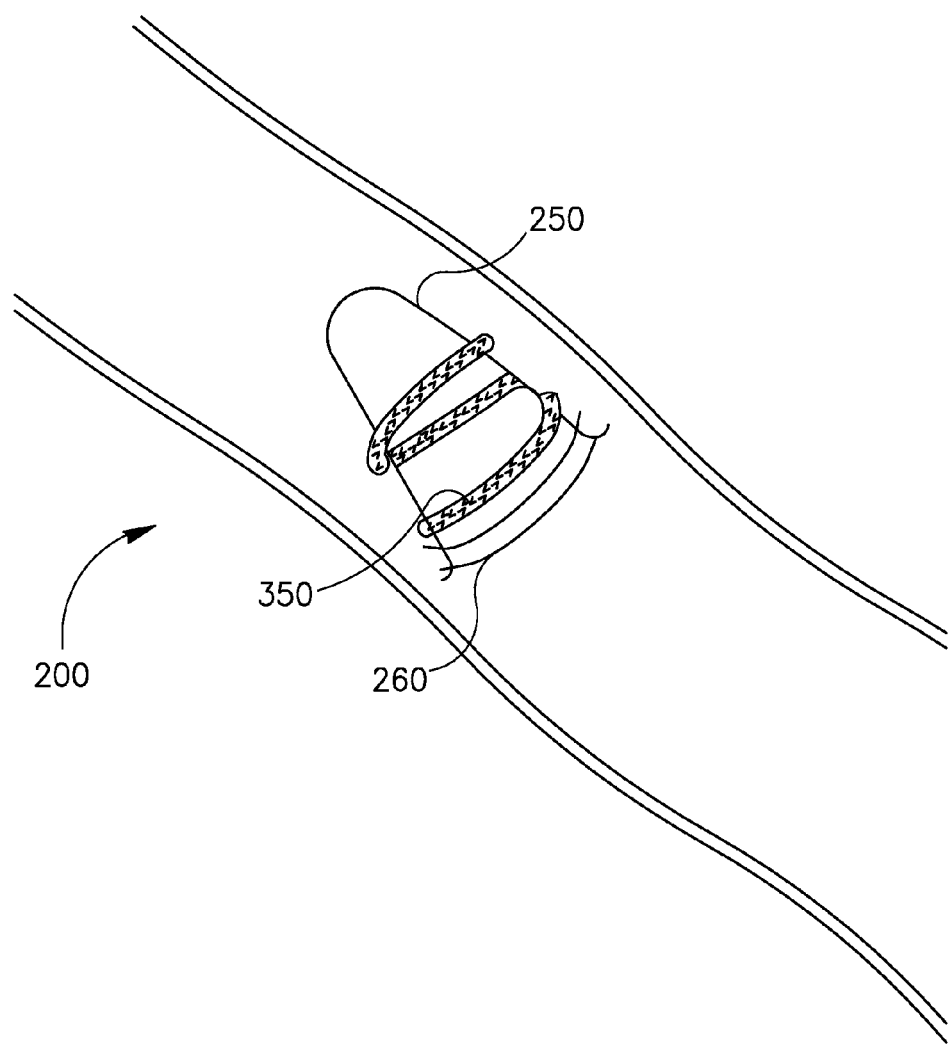
Figure 3E:
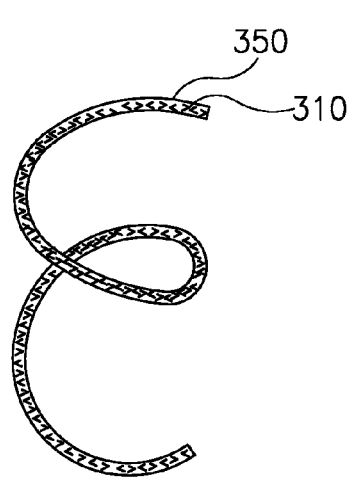

Reference is now made to FIG. 3D, which depicts a coil like mechanism 350 that may be bonded or otherwise connected to vessel blocking device 200. Coil like mechanism 350 may enclose at least a portion of cap 250 and/or base 260, according to some embodiments of the present invention. Coil like mechanism 350 may be expanded by for example balloons 240, cap 250 and/or base 260, optionally providing support to vessel blocking device 200. As can be seen with reference to FIG. 3E, coil-like mechanism 350 may include one or more anchoring mechanisms 310 for anchoring vessel blocking device 200 into the walls of a vessel when stent-like mechanism 340 is expanded sufficiently. Stent-like mechanism 340 may be constructed from metal or other suitable materials.

Figure 4:
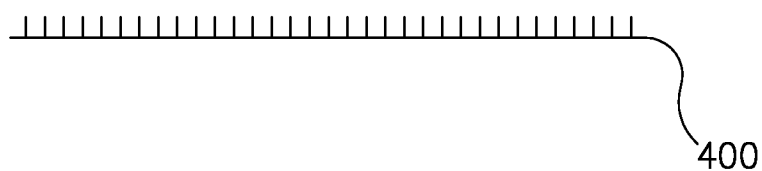
FIGS. 4A-4E are schematic illustrations of anchoring mechanisms on respective substrates, according to some embodiments of the present invention.
Figure 4:
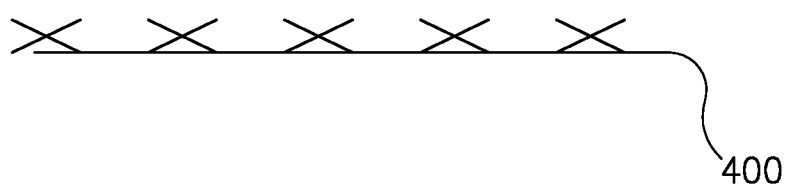
Figure 4:
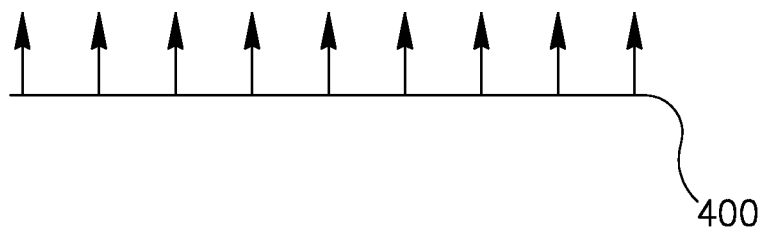
Figure 4:
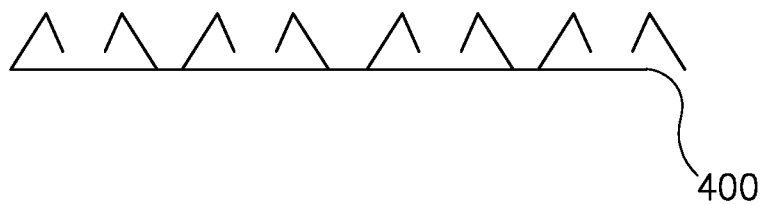
Figure 4:
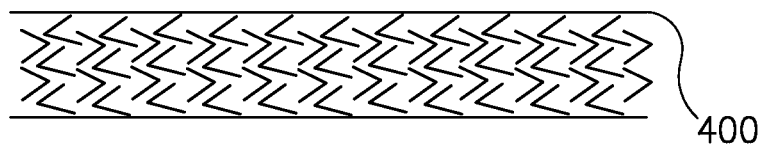

Reference is now made to FIG. 4, which depicts examples 4A-4E of anchoring mechanisms that lie on a substrate 400, according to some embodiments of the present invention. FIG. 4A depicts straight spikes extending from substrate 400. FIG. 4B depicts cross type spikes extending from substrate 400. FIG. 4C depicts hook-like spikes extending outwards from substrate 400. FIG. 4D depicts bent spikes at various angles extending from substrate 400, for example, enabling criss-cross anchoring. FIG. 4E depicts a plurality of spikes that are "locked on" to each other, on substrate 400. Other anchoring mechanisms may be used, using spikes, hooks, pins or other suitable bonding elements. Anchoring mechanisms may be arranged in other suitable arrangements, or in any combination of arrangements. Anchoring mechanisms may be constructed from metal, plastic or any other suitable materials.

Figure 5A:
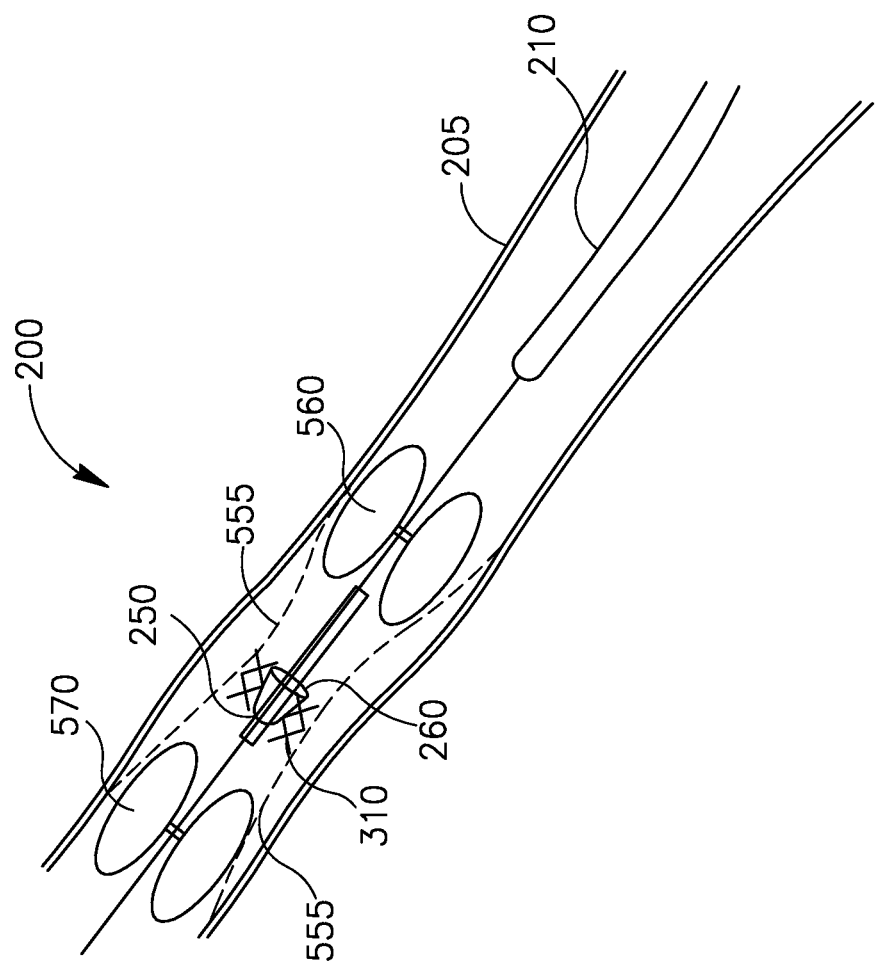
FIGS. 5A and 5B are schematic illustrations depicting the anchoring of respective vessel blocking devices into a vessel wall, using an internal vacuum, according to an embodiment of the present invention.

Reference is now made to FIG. 5A, which depicts a vessel blocking device 200, according to some embodiments of the present invention. Vessel blocking device 200 may include, for example, two balloons or pairs of balloons, for example, 560 and 570, at proximal side and distal side respectively of cap 250. For example, after inflating both sets of balloons, gas and/or liquids may be released through catheter 210. The release of gas and/or liquids may result in a low or relatively low pressure area or a vacuum forming between balloons 560 and balloons 570. The pressure may be low relative to for example the surrounding tissue, or the blood pressure in the nearby sections of the vessel. The vacuum may cause the walls 555 of vessel 205 to be sucked inwards, for example, towards cap 250 and/or base 260, until, for example, anchoring mechanisms 310 anchor themselves into the walls 555 of vessel 205. After cap 250 and/or base 260 have been anchored to walls 555 the balloons may be deflated and catheter 210 may be extracted, together with other non required elements of vessel blocking device 200, leaving required elements of cap 250 and/or base 260 in vessel 205. Any number or type of balloons may be used, in any combination.

Figure 5B:
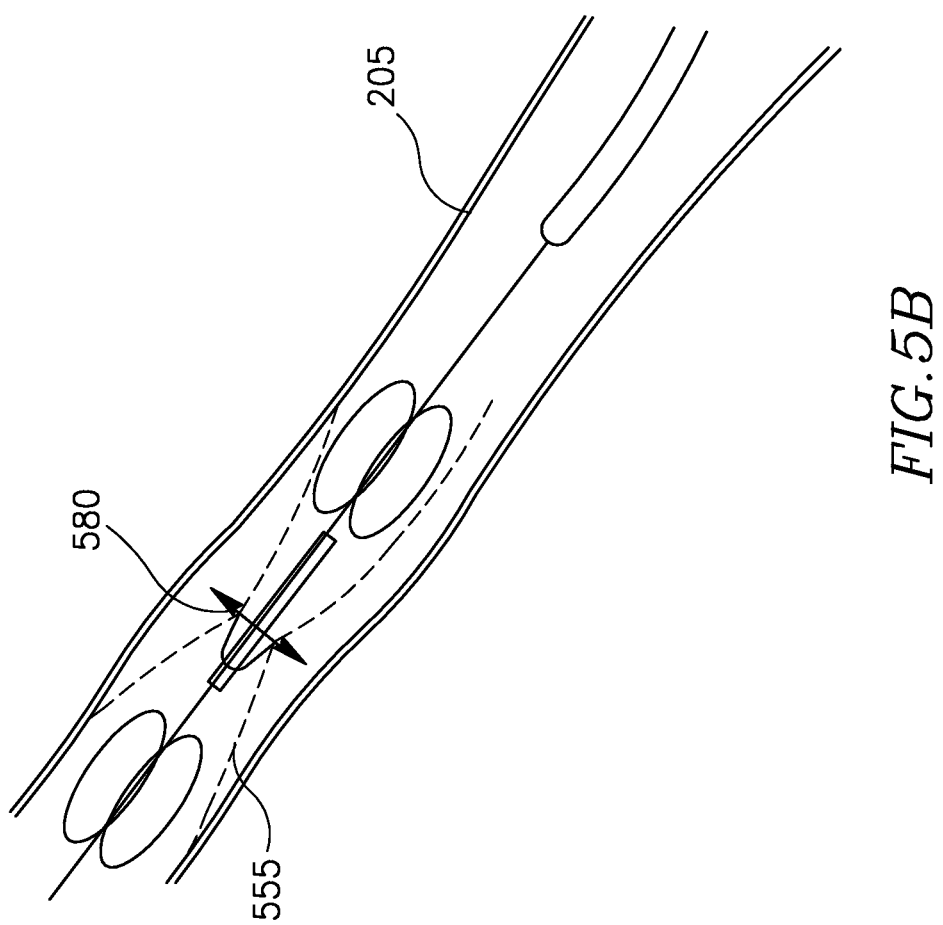

Reference is now made to FIG. 5B which depicts a vessel blocking device 200 being anchored to walls 555 of vessel 205, using hook-type anchoring mechanisms 580. As described above with reference to FIG. 5A, a low or relatively low pressure area or vacuum may be created in an area of vessel 205, therefore causing the vessel walls to be forced inwards until engaging with hooks 580. After cap 250 and/or base 260 have been anchored to walls 555 the balloons may be deflated and the catheter may be extracted, leaving the cap and/or base 260 in vessel 205. Any combination of the above steps may be implemented. Other steps or series of steps may be used.

According to some embodiments of the present invention, a plurality of balloons may be used to generate internal pressure that may cause a vessel to collapse, thereby permanently blocking the vessel. Each of a plurality of vessels may be individually controlled, or may be controlled in groups. For example, balloons may be inflated and deflated to enable control over internal pressure of the vessel, anchoring and de-anchoring of vessel blocking device 200 to the vessel walls, or other suitable functions.

Figure 5C:
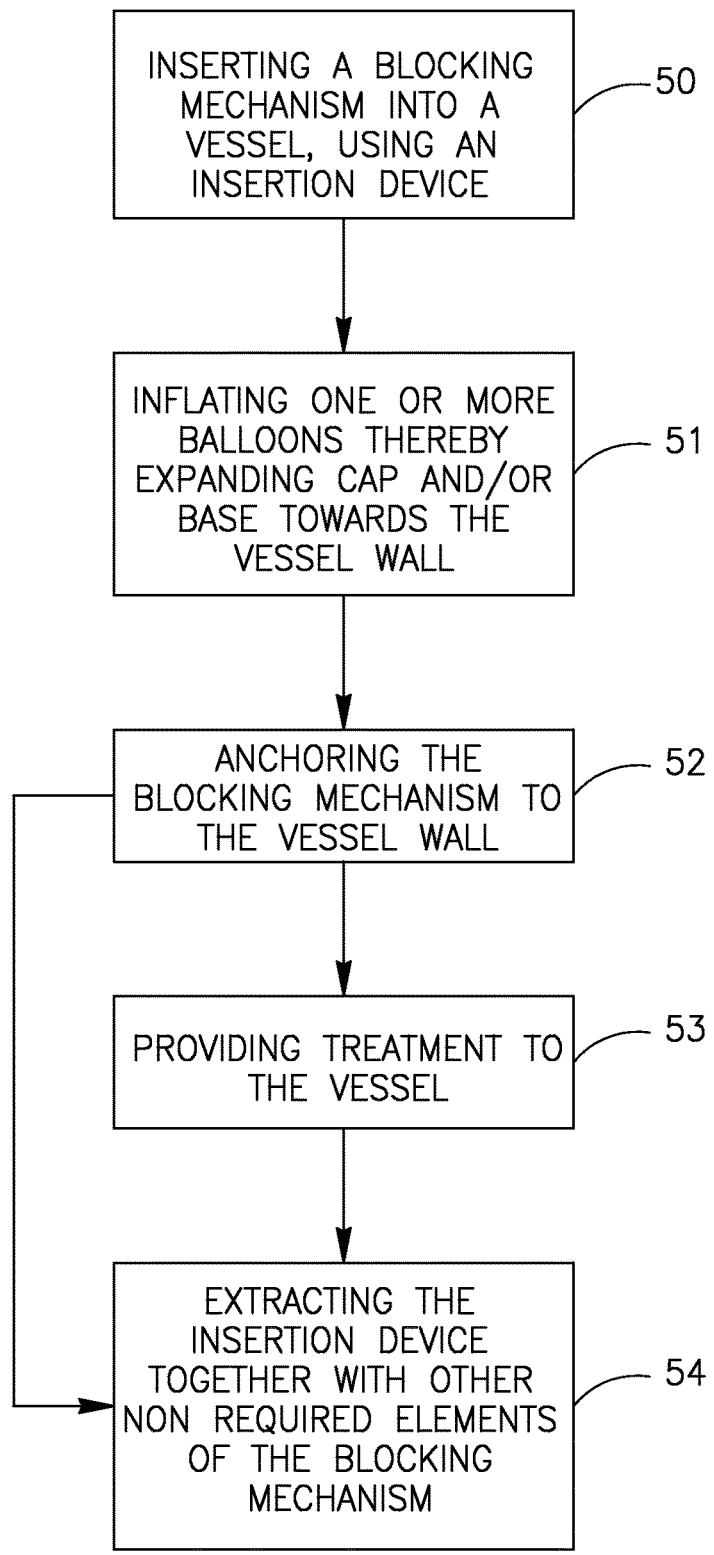
FIG. 5C is a flow chart describing a method for blocking a vessel, according to an embodiment of the present invention.

Reference is now made to FIG. 5C, which is a flowchart of a method for blocking vessels, according to an embodiment of the present invention. In block 50 vessel blocking device (e.g., device 200 of FIG. 2 or other embodiments discussed herein) may be inserted into a vessel (e.g., 205 of FIG. 2) by an insertion device, for example from within a catheter (e.g., 210 in FIG. 2), with elements of vessel blocking device 200 being in a contracted or folded position. Other suitable devices may be used. For example, blocking device 200 may be inserted into a junction of a vessel (e.g., 106 of FIG. 1) where a superficial or another vessel is to be blocked and/or treated. In block 51 one or more balloons (e.g., balloon 240 of FIG. 2) or other expandable devices may be expanded, for example inflated, thereby expanding cap and/or base of blocking device (e.g., cap 250 and/or base 260 of blocking device 200 of FIG. 2) towards the vessel wall. In other embodiments inflation of, for example, at least one balloon may create a vacuum or low pressure area in an area of the vessel which may cause the vessel walls to be forced inwards until engaging with vessel blocking device anchoring mechanism (e.g., anchoring mechanism 310 of blocking device 200 of FIG. 5A) In block 52 cap 250 and/or base 260 may continue to be expanded until piercing, colliding, pressuring etc. the vessel wall, to enable anchoring of vessel blocking device 200 to the vessel wall. In block 53 treatment may be provided to at least a part of vessel 205, for example, sclerotherapy, ligation and/or other suitable treatments or procedures. In block 54 vessel blocking device (e.g., device 200 of FIG. 2) may be disconnected from catheter (e.g., catheter 210 of FIG. 2) and unnecessary elements of vessel blocking device 200 and/or other elements from within vessel 205 may be removed together with catheter 210 from the patient, leaving required elements of vessel blocking device 200 in place in vessel 205. Any combination of the above steps may be implemented. Other steps or series of steps may be used.

Figure 6A:
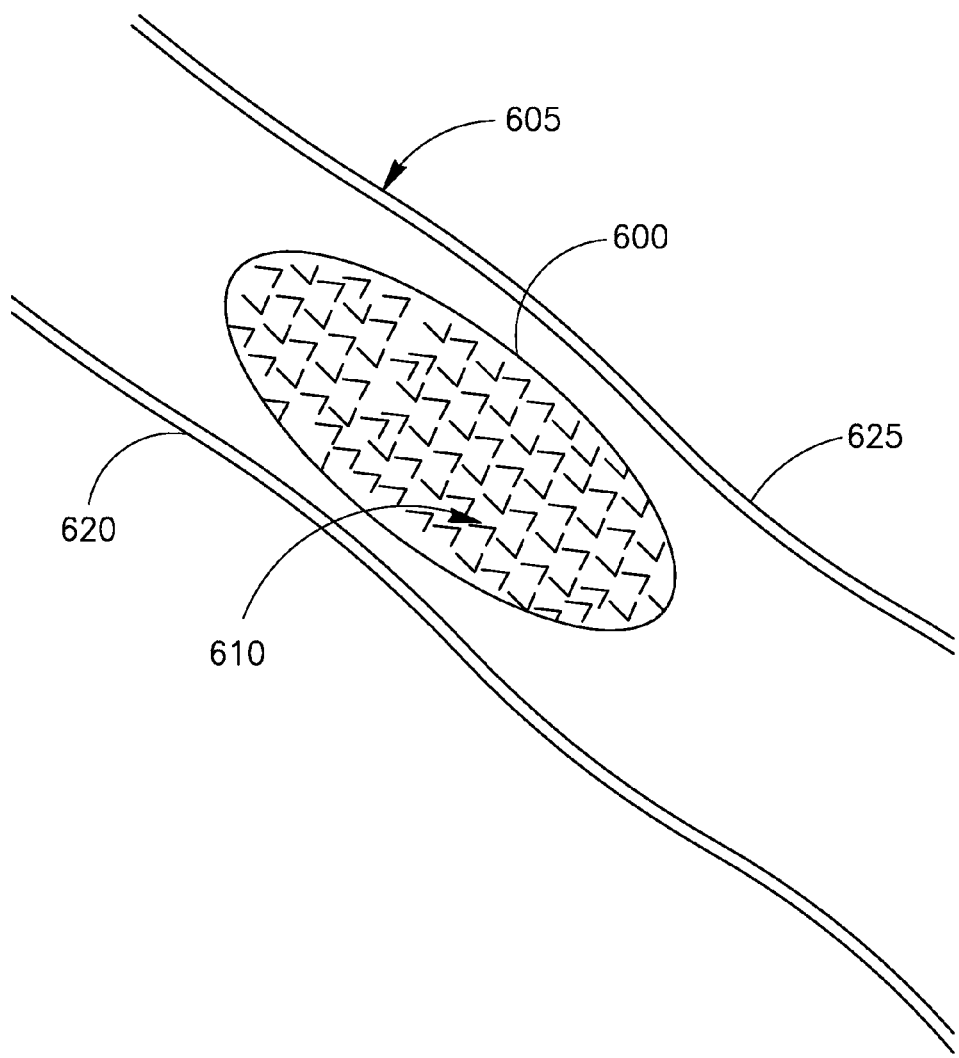
FIGS. 6A-6C are schematic illustrations depicting anchoring of vessel blocking devices into a vessel wall, according to some embodiments of the present invention.

Reference is now made to FIG. 6A which is a schematic illustration of a vessel blocking device according to some embodiments of the present invention. A vessel blocking device may be a collapsible or reversible device, for example, which is able to change its shape and to return to the former shape. Collapsible plug or blocking device 600, which may be constructed from stainless steel, Nitinol, biodegradable polypropylen, plastic material for use inside blood vessels, or any other suitable materials, may be delivered in a collapsed or folded state from within a delivery capsule, a catheter or alternative delivery device, for example, within a guide wire or guide balloon of a catheter etc. Plug 600 may be expandable into any suitable shape to fit within a vessel 605 (e.g., a varicose vein), and to be substantially lodged between walls of a vessel at a target location. For example, plug 600 in its expanded form may have a ring shape, oval, figure-8 (e.g., FIG. 6B) or another suitable shape. Plug 600 may include an interconnected or mesh type architecture that is known in the art of stenting. Other suitable architectures may be used. Plug 600 may include clasps, fasteners, hooks 610 or other suitable locking or catching elements to enable engaging, catching, fastening, dragging or otherwise locking plug 600 to walls of vessel 605. Hooks 610 may be configured to be directed in multiple directions to enable locking of plug 600 to walls of vessel 605 in multiple directions and locations. For example, hooks may be configured like Velcro™ or other suitable fastening tape, consisting of, for example, a strip of nylon with a surface of minute hooks that fasten to a corresponding strip with a surface of uncut pile. In one embodiment, hooks 610 may be directed to face left wall 620 and right wall 625 of vessel 605 (left and right being relative terms, and being used for the point of view shown), such that when pressure is applied externally to vessel 605, adjacent to plug 600, hooks 610 may engage both left wall 620 and right wall 625, and/or both ceiling and floor of the vessel, thereby fusing the vessel walls together, optionally around plug 600. Hooks may be configured in other directions, to enable sealing of plug 600 to vessel 605 at one or more locations.

Figure 6B:
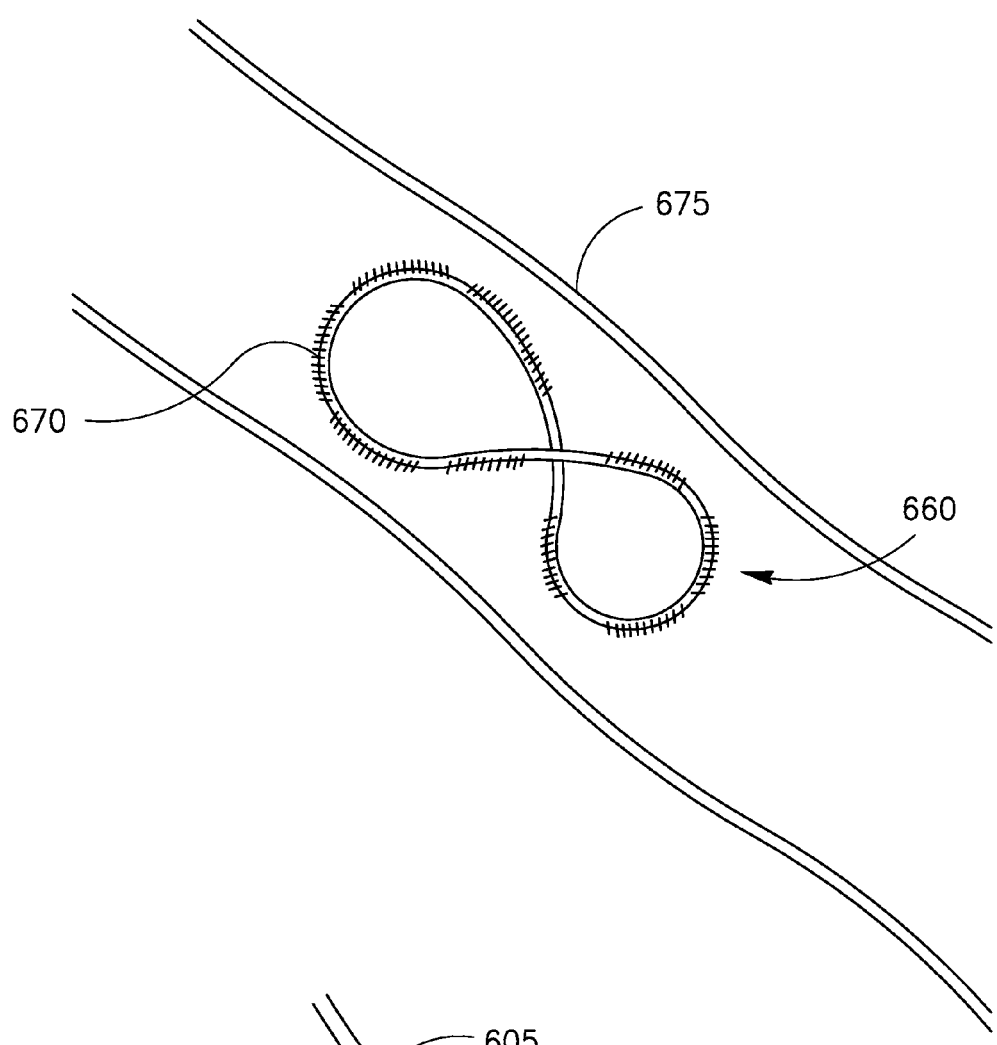

As can be seen with reference to FIG. 6B, a target area of a vessel, for example a selected junction in a bifurcated vein, may be blocked by vessel blocking device which may include a plug 660 constructed from a memory material, for example, Nitinol or other suitable materials. Memory plug 660 may be delivered in a collapsed or folded state from within a delivery capsule, a catheter or alternative delivery device, for example, within a guide wire or guide balloon of a catheter etc. Memory plug 660 may be expanded after delivery to a selected area, such that the plug may engage the walls of vessel 675. Memory plug 660 may include hooks 670 or other suitable locking or catching elements to enable engaging, catching, or otherwise locking plug 660 to vessel walls 675. Hooks 670 may be configured to be directed in one or more directions to enable locking of plug 660 to walls of vessel 675. Upon engagement of the vessel walls, memory plug 660 may return to a predetermined shape, for example, a flat shape that enables the walls of the vessel to be blocked, fused or sealed around plug 660. For example, by applying pressure externally to vessel 675, adjacent to plug 660, hooks 670 may engage vessel walls 675 and may fuse and/or connect vessel walls together, around plug 660. For example, a doctor or a health professional may press outside the body in proximity to the plug 660 location and may cause plug 660 to flatten and/or collapse.

Plug 660 may be constructed from absorbable and/or dissolvable materials which may dissolve in the body after a certain period of time which may increase the encapsulation in the treatment area, for example, the saphenofemoral junction area, and may prevent recanalization.

Figure 6C:
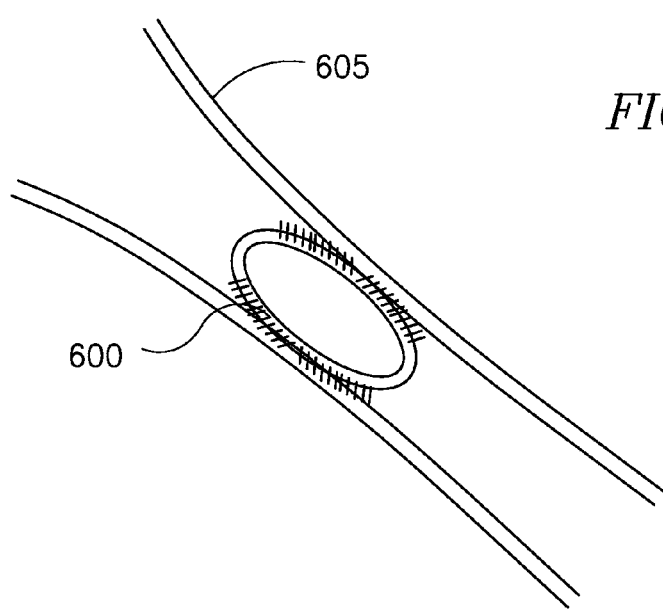

As can be seen with reference to FIG. 6C, plug 600 in its collapsed, folded or pressured state may permanently fasten the walls of vein 605 together, optionally joining the walls by being fused to plug 600, thereby providing a sealed zone or area in which treatment may be applied. An outside pressure may be applied to plug 600 when it is placed in the preferred position in the vessel and may result in engagement and/or collapsing of the vessel walls towards plug 600, by for example, hooks or other anchoring mechanism. This may enable blocking or occluding of a vessel. Plug 600 may be naturally expandable, collapsible, may be a memory shape material, or may have other suitable shapes and/or designs to enable forming of a sealed zone in a vessel.

Figure 6D:
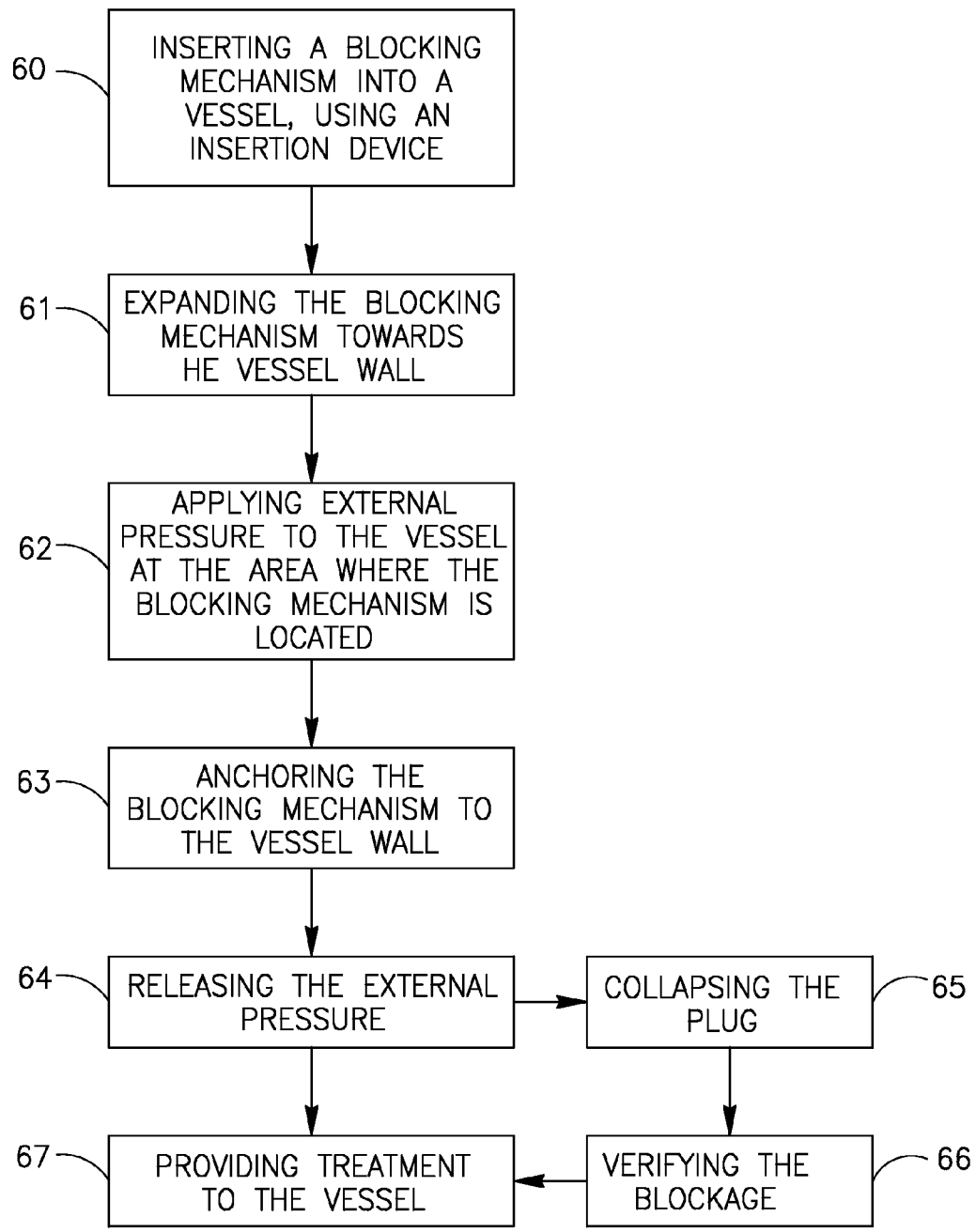
FIG. 6D is a flow chart describing a method for blocking a vessel, according to another embodiment of the present invention.

Reference is now made to FIG. 6D, which is a flowchart of a method for blocking vessels using collapsible plug or blocking device, according to an embodiment of the present invention. In block 60, a plug in collapsed, minimized or shrunken form may be delivered to a selected location using, for example, a delivery catheter, and optionally using ultrasonic scanning to determine the selected location. In block 61 the plug may be expanded, for example, using a balloon or other suitable mechanisms. In block 62 pressure may be applied externally to the vessel at the area which is in proximity to the selected location to allow engagement of the locking mechanisms to the vessel walls. In block 63 hooks or other locking mechanisms may engage the vessel walls by fusing the vessel walls together, optionally around the plug. For example, locking mechanisms may anchor and/or connect the blocking plug to the vessel wall and external pressure may change the shape of the plug and may create an obstruction of the vessel. In block 64 the external pressure may be released. In block 65 the plug may be permanently collapsed to provide a seal or a block at the selected location in the vessel. In block 66 the vessel blockage may be verified, for example, using ultrasonic scanning or any other verifying technique. In block 67 treatment may be applied to the treatment area, which may be defined by the positioning of the plug. Other steps and series of steps, may be used, and certain steps may be omitted.

Figure 7A:
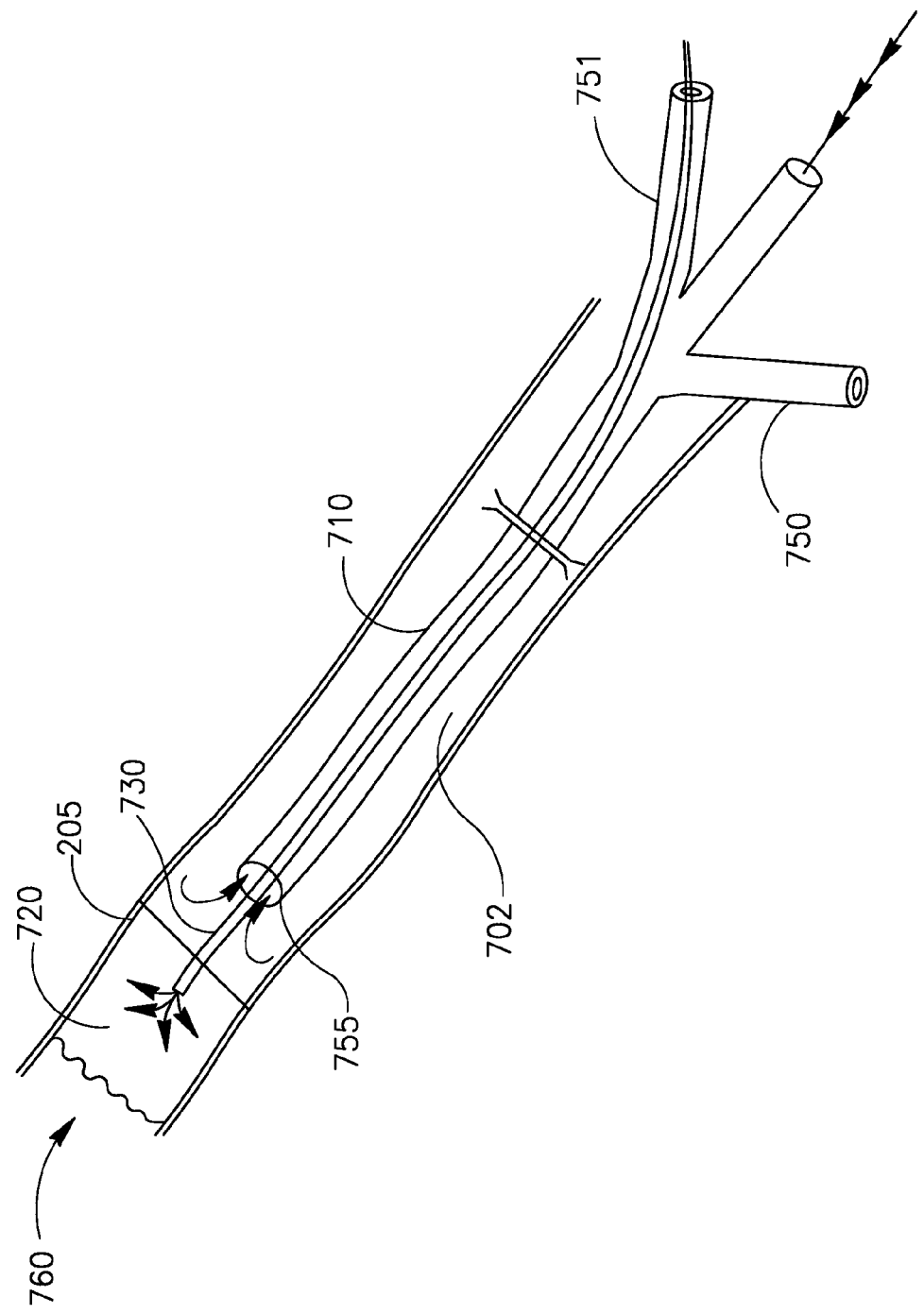
FIG. 7A is a schematic illustration depicting the anchoring of a vessel blocking device into a vessel wall, according to an embodiment of the present invention.

Once the selected vessel or junction has been blocked, the vessel upstream of the blockage may be treated. For example, device 200 of FIG. 2 and/or other suitable devices may be used to ligate the segment while significantly limiting the risk of embolic damage, and optionally while inflicting minimal trauma to the surrounding tissue. Additionally or alternatively a sclerosing agent may be delivered to the segment distal to the ligation, using for example a drug catheter. The agent delivery may be done while suction of blood through catheter 210 to generate zero pressure. The zero pressure may prevent the sclerosing agent to penetrate other vessel. Such a sclerosing agent or other suitable agents may be dispersed at the distal tip 220 of device 200 or at other suitable locations. Other steps or series of steps may be used Reference is now made to FIG. 7A which is a schematic illustration of a pressure control mechanism according to an embodiment of the present invention. After insertion of plug or blocking device 760 into vessel 205 a treatment area 720 may exist between the blocking device 760 and the distal tip of catheter 710. Delivery of a sclerosing or other suitable agent into a vessel may cause increased pressure within treatment area 720. Sclerosing or other suitable agent may be delivered into treatment area 720 through a small diameter catheter 730 or other suitable device which may be inserted through catheter 710 port 751 and may reach the distal end 755 of catheter 710. Increased pressure may, for example, enable the sclerosing agent to penetrate tributaries of the vein or other undesired locations, thereby entering the blood stream of the patient. Internal vein pressure may be controlled using a suction device to selectively remove contents from the vein. For example, suction device or port 750, which may be, for example, a syringe, suction pump, balloon device or other suitable devices which may be used to draw or pump out contents, for example blood, from around the distal end 755 of catheter 710, to reduce the pressure in treatment area 720. In one embodiment suction device 750 may be operated synchronously with the delivery of sclerosing agent through, for example, port 751 and inner catheter 730, to remove a similar quantity of contents as in being infused, thereby maintaining the pressure in treatment area 720. In other embodiments suction 750 may be used to maintain minimal, low, or zero pressure in treatment area 720, to reduce the entry of sclerosing agents into the blood stream, external to treatment area 720. Further, other steps or series of steps may be used.

Figure 7B:
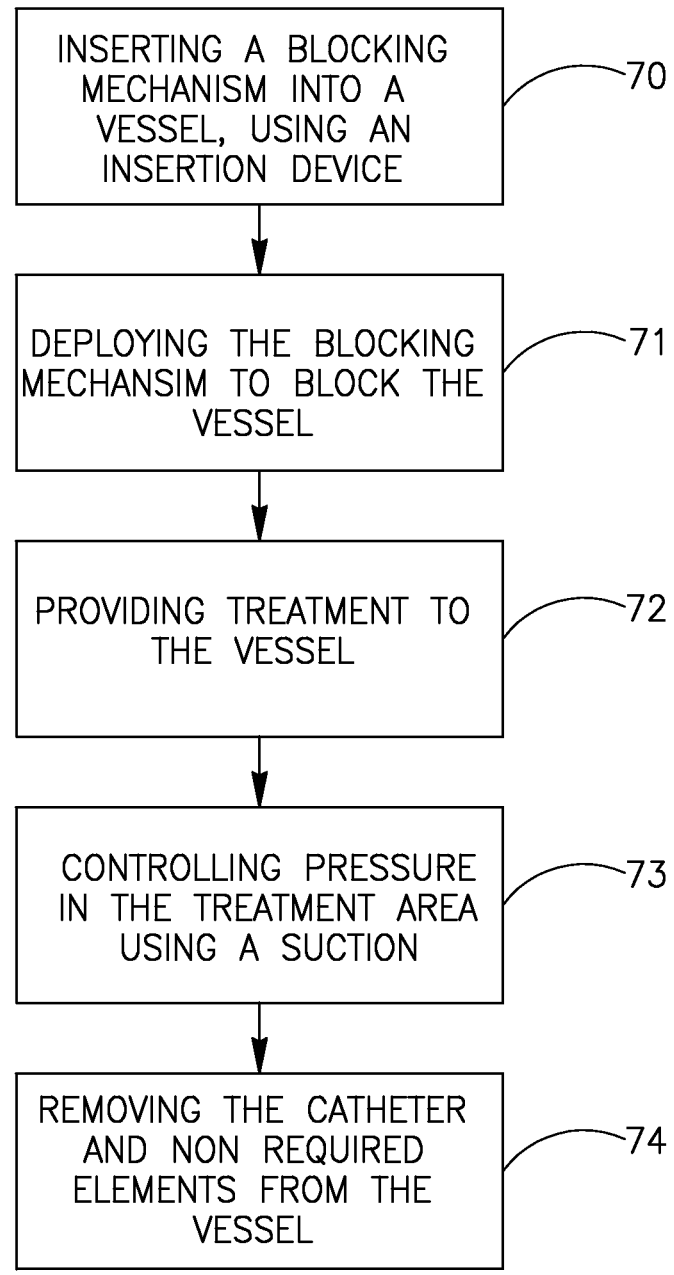
FIG. 7B is a flow chart describing a method for blocking a vessel, according to an embodiment of the present invention.

Reference is now made to FIG. 7B, which is a flowchart describing a method for blocking vessels and providing treatment to vessels, according to an embodiment of the present invention. In block 70, a plug or blocking device in collapsed form may be delivered to a selected location using, for example, a delivery catheter. Ultrasonic scanning may be used to determine the selected location, and to monitor the delivery of the plug to the selected location. In block 71 the plug or blocking device may be deployed, for example expanded, using a balloon or other suitable mechanisms, for example by radial forces restrained in the collapsed form, to block the selected vessel (as described in detail above). In block 72 treatment may be applied to the treatment area, which may be defined by the positioning of the plug. For example, sclerosing or other agents may be dispensed to close the selected vessel, for example, sclerosing agents may be inserted into the blocked area through a catheter. In block 73 a suction device (e.g., suction device 750 of FIG. 7A) may draw contents, for example blood from a vessel, for example, adjacent to the distal end 755 of catheter 710 of FIG. 7A. The suction may enable for example control of the pressure inside the treatment area. For example, suction device (e.g., suction device 750 of FIG. 7A) may be operated synchronously with the delivery of sclerosing agent to remove a similar quantity of contents as in being infused, thereby maintaining the pressure in treatment area (e.g., treatment area 720 of FIG. 7A). In other embodiments, reduction in pressure, for example, suction may be used to maintain minimal, low, or zero pressure in treatment area, to reduce the entry of sclerosing agents into the blood stream, external to treatment area. In block 74 the catheter and the various components that are not intended to remain in the vessel may be pulled out of the vessel. The plug, together with the sclerosing agents may be left in the vessel, to destroy or close the unwanted vessel, and to seal off the vessel such that the sclerosing agent cannot flow though the vessel into the blood stream. Further, other steps or series of steps may be used.

Figure 7C:
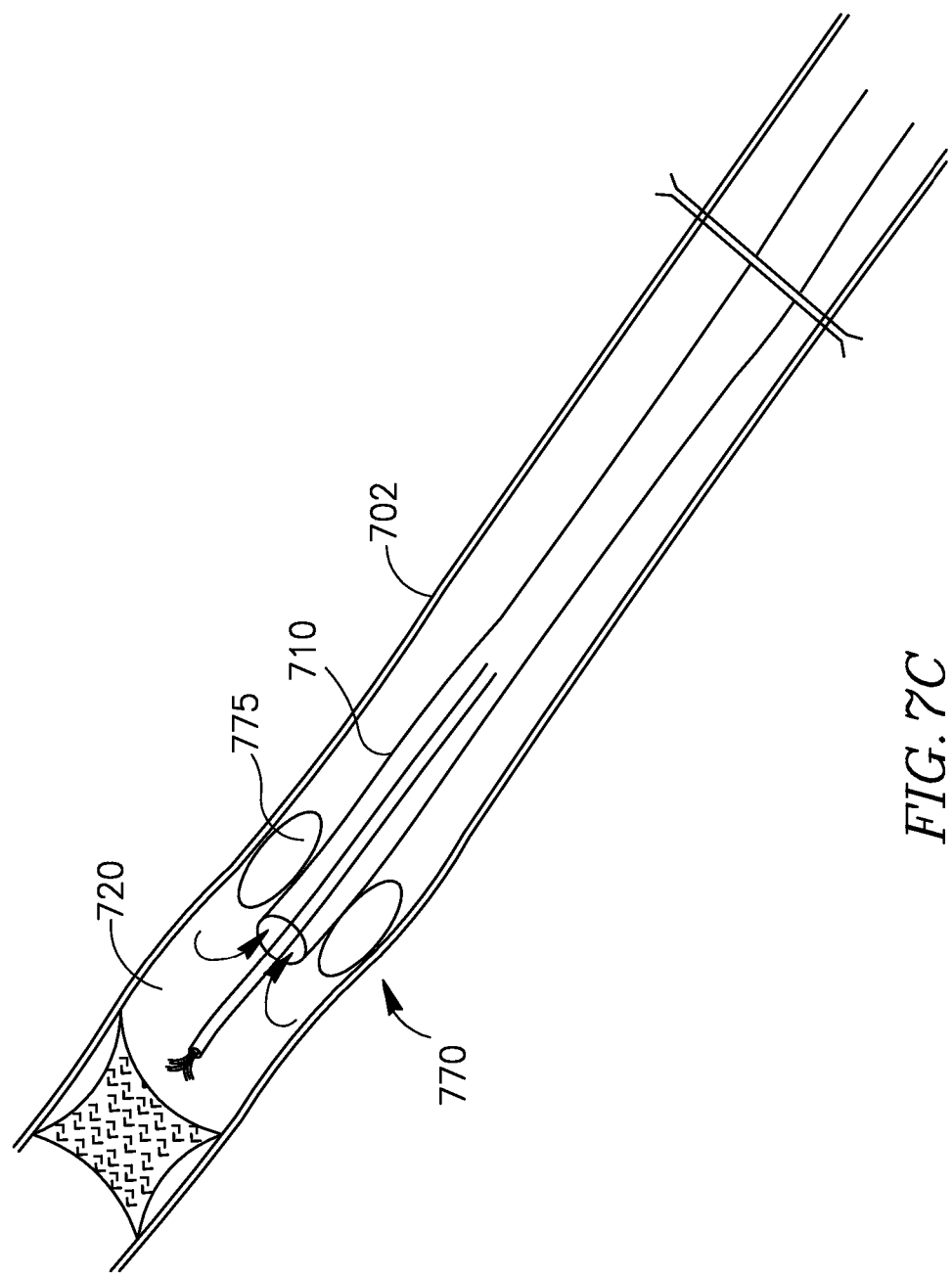
FIG. 7C is a schematic illustration depicting the anchoring of a vessel blocking device into a vessel wall, according to an embodiment of the present invention.

Reference is now made to FIG. 7C, which is a schematic illustration of a pressure reducing device according to some embodiments of the present invention. Delivering of a sclerosing or other suitable agent into a vessel may cause increased pressure within a treatment area (e.g., treatment area 720 of FIG. 7A). Increased pressure may, for example, enable the sclerosing agent to penetrate tributaries of the vein or other undesired locations, thereby entering the blood stream of the patient. A pressure reducing device 770, which may include, for example, one or more expandable/collapsible balloons 775, may be used to push and/or pull out contents, for example blood, from vein/vessel 702, to reduce the pressure in treatment area 720. For example, balloon(s) may be pulled out of vessel by extracting catheter 710 from vessel 702. In one embodiment pressure reducing device 770 may be operated synchronously with the delivery of sclerosing agent, to remove a similar quantity of contents as in being infused, thereby maintaining the pressure in treatment area 720. In other embodiments pressure reducing device 770 may be used to maintain minimal, low, or zero pressure in treatment area 720, to reduce the entry of sclerosing agents into the blood stream, external to treatment area 720.

Figure 8:
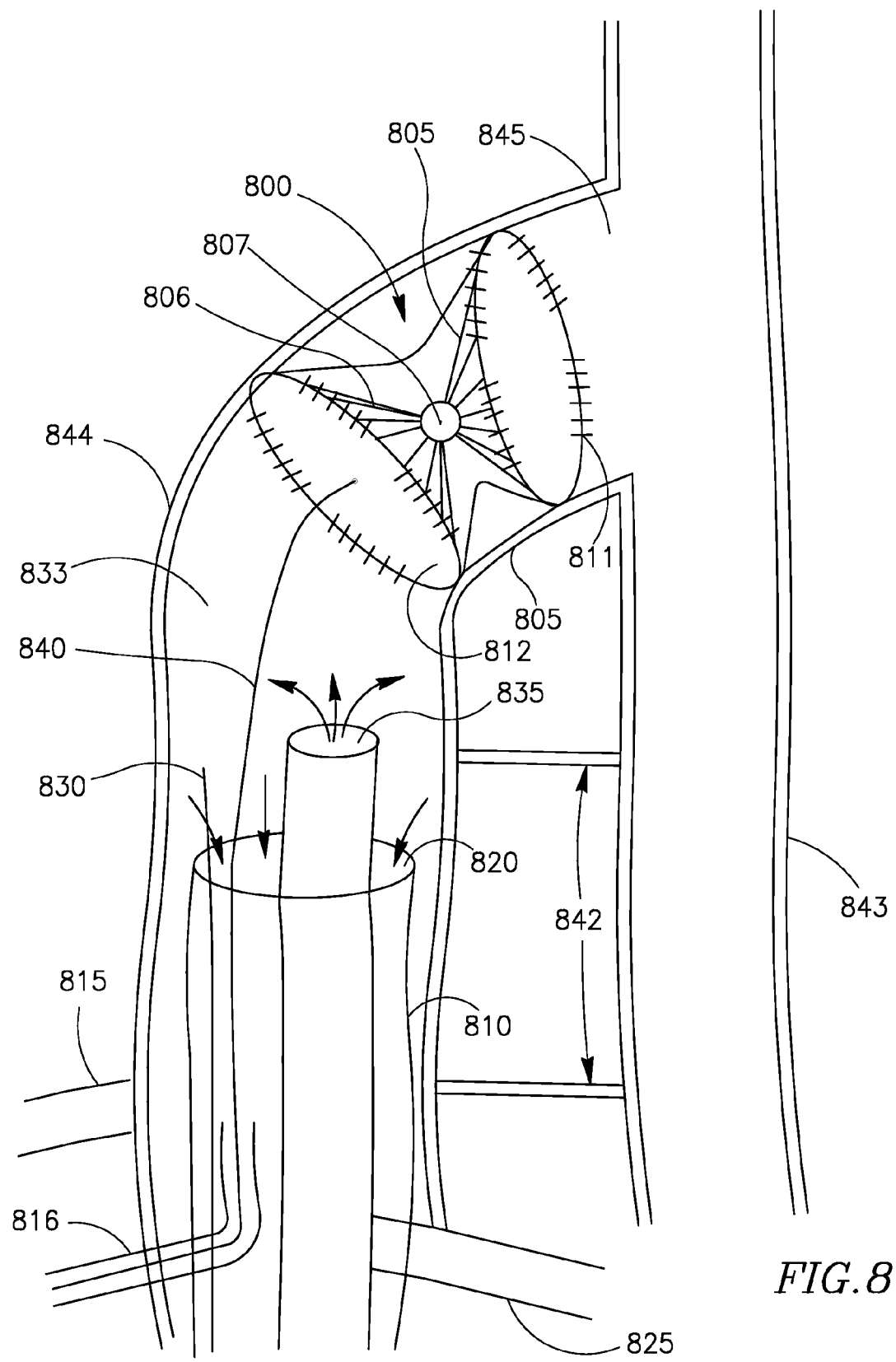
FIG. 8 schematic illustration of a transverse view of an intraluminal vessel occluding stent or blocking device 800 according to an embodiment of the present invention.

Reference is made to FIG. 8, which schematically illustrates a transverse view of an intraluminal vessel occluding stent or blocking device 800 according to an embodiment of the present invention. Occluding stent 800 may be inserted, for example, into a target vessel 805 that requires treatment, for example, a safenus vein, a bifurcated vessel or an occluded blood segment that is to be blocked and/or otherwise treated, or the saphenofemoral junction area 845 between a deep vein 843 and safenus vein 805. Other suitable areas may be treated. The target vessel 805 may be connected to another vessel, for example, as the safenus vein is connected to the deep vein by plurality of perfurant veins 842. Such insertion of occluding stent 800 may be implemented, for example, using an insertion device, for example, catheter 810, which may include a guidewire 830, to help guide occluding stent 800 to a selected location. Occluding stent 800 may be inserted into vessel 805 through catheter 810 in its compact, collapsed or minimized form or shape. After catheter 810 is positioned in the treatment area occluding stent 800 may be released into the vessel by a catheter 810 pusher, or additional catheter 835, which may be a thinner lumen catheter relative to catheter 810 and may be inserted inside catheter 810 lumen (not shown). When occluding stent 800 is out of catheter 810 it may expend towards the vessel walls and may change its shape. Other insertion devices and methods may be used.

Catheter 835 may include for example a drug dispensing mechanism 825, to enable delivery of a pharmaceutical compound, medication or agent, herein referred to as a sclerosing agent, to a target area. Catheter 810 may include a distal tip 820 which may be located in proximity to the blocking area. Vessel occluding stent or blocking device 800 may be expandable into an hourglass shape, or into the shape of two cones 805 and 806 or other concave, bowl or hemispherical shaped devices, typically connected or attached at their narrow ends to fit within vessel 805 (e.g., a varicose vein), and to substantially be lodged between walls of a vessel at a target location. Other shapes may be used. For example, vessel occluding stent 800 in its expanded form may have the shape of two cones, where the upper cone may prevent blood from penetrating the treatment area 833 while the lower cone may prevent sclerosing agents from entering into the blood stream, external to treatment area 833. Upper and lower are relative terms when used herein; lower generally means in proximity to the insertion device insertion point. Vessel occluding stent 800 may include an interconnected or mesh type architecture that is known in the art of stenting. Other suitable architectures may be used. Vessel occluding stent 800 may be constructed from stainless steel, graft, film, Nitinol, biodegradable polypropylen, plastic material for use inside blood vessels, or other suitable materials. Vessel occluding stent 800 may be constructed from absorbable and/or dissolvable materials which may dissolve in the body after a certain period of time and may increase the encapsulation in the treatment area, for example, the saphenofemoral junction area 845, and may prevent recanalization. Vessel occluding stent 800 may be delivered in a collapsed state from within a delivery capsule or alternative delivery device, for example, within a guide wire or guide balloon of a catheter etc.

Vessel occluding stent 800 may include clasps, fasteners, hooks 811 and/or 812 or other suitable locking or catching elements to enable engaging, catching, fastening, dragging or otherwise locking vessel occluding stent 800 to vessel walls 805. Hooks 811 and/or 812 may be configured to be directed in multiple directions to enable locking of vessel occluding stent 800 to walls of vessel 805 in multiple directions and locations. For example, hooks may be configured like Velcro™ or other suitable fastening tape, consisting of, for example, a strip of nylon with a surface of minute hooks that fasten to a corresponding strip with a surface of uncut pile. Hooks may be configured in other directions, to enable sealing of vessel occluding stent 800 to vessel 805 at one or more locations. Other fastening or fixing methods may be used.

Vessel occluding stent 800 may include floss or a wire 840, for example, a medical suture type which may be absorbable and may dissolve in the body after a limited period of time. For example, the suture may be made of biocompatible material. Wire 840 may be coated with occluding agent, for example, fibrin, sclerosant or any other suitable occluding material. Wire 840 may be connected to the lower cone 806 of vessel occluding stent 800 or to any other point of vessel occluding stent 800 and may come out of port 816 of catheter 810 or may be released while pulling of catheter 810 pusher or catheter 835 out of catheter 810. Wire 840 may be used to guide and lead device 800 to a selected location. Wire 840 may be used to prevent migration or movement of vessel occluding stent 800 inside vessel 805 until hooking mechanism 811 and/or 812 is engaged with vessels walls 805. In addition wire 840 may be used in emergency situation for pulling the vessel occluding stent 800 out of vessel 805.

After insertion of vessel occluding stent 800 into vessel 805 a treatment area 833 may exist between the occluding stent 800 and the distal tip 820 of catheter 810. Delivering of a sclerosing or other suitable agent into a vessel while pulling out catheter 810 and/or catheter 835 may cause increased pressure within treatment area 833. Sclerosing or other suitable agent may be delivered into treatment area 833 through a catheter 835 or other suitable device which may be inserted through port 825 and may reach the distal end 820 of catheter 810 and treatment area 833. Increased pressure may, for example, enable the sclerosing agent to penetrate tributaries of the vein or other undesired locations, thereby entering the blood stream of the patient, for example, via perforant veins 842. Internal vein pressure may be controlled using a suction device to selectively remove contents from the vein. For example, suction device or port 815, which may be, for example, a syringe, suction pump, balloon device or other suitable devices which may be used to draw or pump out contents, for example blood, from around the distal end 820 of catheter 810, to reduce the pressure in treatment area 833. In one embodiment suction device 815 may be operated synchronously with the delivery of sclerosing agent through, for example, port 815 and inner catheter 835, to remove a similar quantity of contents as in being infused, thereby maintaining the pressure in treatment area 833. In other embodiments controlling the pressure in the treatment area may include reduction in pressure in the treatment area, for example, suction 815 may be used to maintain minimal, low, or zero pressure in treatment area 833, to reduce the entry of sclerosing agents into the blood stream, external to treatment area 833. Further, other steps or series of steps may be used.

According to some embodiments of the present invention, after extracting catheter (e.g., catheter 210 of FIG. 2) or other input device from a vessel (e.g., vessel 205 of FIG. 2), a hole may be left by the extraction of catheter guidewire (e.g., guidewire 230 of FIG. 2). Such a hole, gap or opening, etc., may be partially or completely blocked, for example, using a plug or other suitable blocking element to enable cap (e.g., cap 250 of FIG. 2) to seal vessel 205.

Although some embodiments of the invention described above may refer to an intraluminal device configured for vessel ligation, it will be appreciated by those skilled in the art that the intraluminal device according to other embodiments of the invention may be configured for ligating other bifurcated lumen, artery or vessel, e.g., in the vascular, biliary, genitourinary, gastrointestinal, nervous and respiratory systems, which may have narrowed, weakened, distorted, or otherwise deformed structures. Other lumens may be blocked.

The foregoing description of the embodiments of the invention has been presented for the purposes of illustration and description. It is not intended to be exhaustive or to limit the invention to the precise form disclosed. It should be appreciated by persons skilled in the art that many modifications, variations, substitutions, changes, and equivalents are possible in light of the above teaching. It is, therefore, to be understood that the appended claims are intended to cover all such modifications and changes as fall within the true spirit of the invention.

What is claimed is:

1. A vessel blocking device comprising:
   an expandable cap adapted to block a vessel having an bottom and an opening; and
   an anchoring mechanism having a plurality of catching elements connected to a rim of said opening of said expandable cap and adapted to engage with a vessel wall of said vessel, wherein each one of said plurality of catching elements comprises an array of angled spikes pointing toward a plane crossing said bottom perpendicularly to a longitudinal axis of said expandable cap; and
   a hook shaped mechanism mechanically connected to said expandable cap at said bottom and adapted to be connected to an extraction hook or wire;
   wherein said hook shaped mechanism having a first end connected to said bottom of said expandable cap, and a second end adapted to be connected to said extraction hook or said wire, wherein said second end radiates from said first end towards said opening; and
   wherein the hook shaped mechanism has an extraction hook encircled by said expandable cap.

2. The vessel blocking device of claim 1, wherein said expandable cap comprises a concave blocking element.

3. The vessel blocking device of claim 2, wherein the hook shaped mechanism is connected at the bottom of said concave blocking element.

4. The vessel blocking device of claim 1, wherein the vessel blocking device is delivered into said vessel in a folded state.

5. The vessel blocking device of claim 1, further comprising a base, wherein the blocking device is located at the distal tip of an insertion device and a balloon being disposed between the expandable cap and said base.

6. The vessel blocking device of claim 1, wherein the expandable cap is concave, and wherein the expandable cap is expandable so that a rim of the expandable cap extends outwards towards vessel walls.

7. The vessel blocking device of claim 1, further comprising a base expandable outwards towards vessel walls.

8. The vessel blocking device of claim 1, wherein an increase in pressure in the inner portion of the expandable cap causes the cap to expand outwards towards the vessel walls.

9. The vessel blocking device of claim 8, wherein pressure is provided by balloon inflation.

10. The vessel blocking device of claim 1, wherein pressure stored within the expandable cap expands outwards towards the vessel walls.

11. The vessel blocking device of claim 10, wherein pressure is provided by a stent like mechanism.

12. The vessel blocking device of claim 10, wherein pressure is provided by a coil like mechanism.

13. The vessel blocking device of claim 1, further comprising a base, wherein said base comprises an anchoring mechanism to anchor the expandable cap to the vessel walls.

14. The vessel blocking device of claim 13, wherein anchoring mechanism comprises a rim expandable towards a vessel.

15. The vessel blocking device of claim 1, comprising an absorbable wire.

16. The vessel blocking device of claim 15, wherein the absorbable wire is coated with occluding agent.

17. The vessel blocking device of claim 1, wherein said catching elements are adapted to be locked in the vessel wall.

18. The vessel blocking device of claim 1, wherein the device is sized and shaped for implantation within a vessel.

19. The vessel blocking device of claim 1, wherein the device is constructed from biodegradable materials.

* * * * *